United States Patent [19]

Tompkins et al.

[11] Patent Number: 5,785,647
[45] Date of Patent: Jul. 28, 1998

[54] SURGICAL INSTRUMENTS USEFUL FOR SPINAL SURGERY

[75] Inventors: Christine M. Tompkins, Fairfield; Peter W. J. Hinchliffe, New Haven; Scott W. Larsen; Christopher McDonnell, both of Newtown, all of Conn.

[73] Assignee: United States Surgical Corporation, Norwalk, Conn.

[21] Appl. No.: 690,689

[22] Filed: Jul. 31, 1996

[51] Int. Cl.[6] ............................................. A61B 1/22
[52] U.S. Cl. ........................... 600/201; 600/204; 606/205
[58] Field of Search ............................... 600/201, 204, 600/206, 210, 213, 214, 215, 216, 217, 219, 225, 226, 235; 606/60, 61, 72, 78, 167, 205, 206, 207

[56] References Cited

U.S. PATENT DOCUMENTS

| | | | |
|---|---|---|---|
| 5,514,157 | 5/1996 | Nicholas et al. | 600/204 X |
| 5,577,993 | 11/1996 | Zhu et al. | 600/204 |

Primary Examiner—Beverly M. Flanagan

[57] ABSTRACT

An apparatus for use during endoscopic discectomy procedures includes an elongated portion defining a generally longitudinal axis and having proximal and distal ends, a retractor mechanism disposed at the distal end of the elongated portion and having at least two retractor members for engaging and spreading tissue, an articulating mechanism operatively connected to the retractor mechanism for selectively articulating the two retractor members and an actuator mechanism operatively connected to the retractor mechanism for causing relative movement between the two retractor members. The retractor mechanism is preferably releasably mounted to the distal end of the elongated portion and is released by a release mechanism. The apparatus further includes a tissue penetrating member associated with the retractor mechanism and mounted for movement to facilitate mounting of the retractor mechanism to tissue. The tissue penetrating member is mounted to the distal end of the elongated portion and is movable between a non-deployed position and a deployed position. A deployment mechanism for moving the tissue penetrating member to the deployed position is provided. A method for facilitating the retracting of tissue during a surgical procedure is also disclosed.

42 Claims, 29 Drawing Sheets

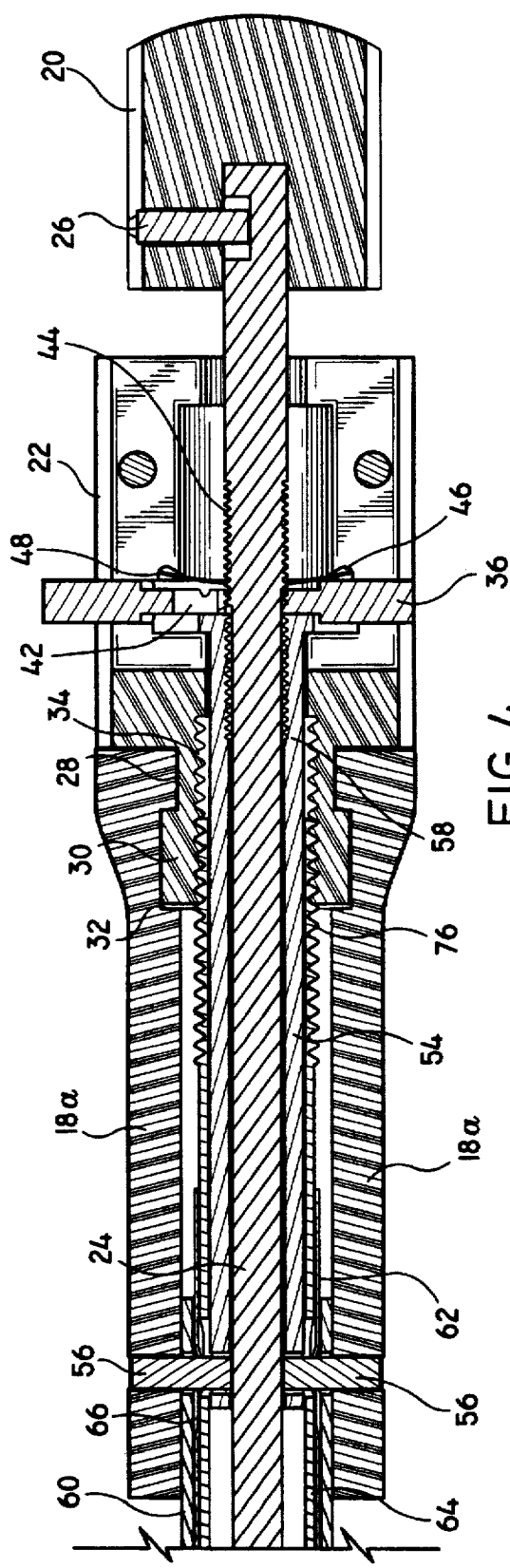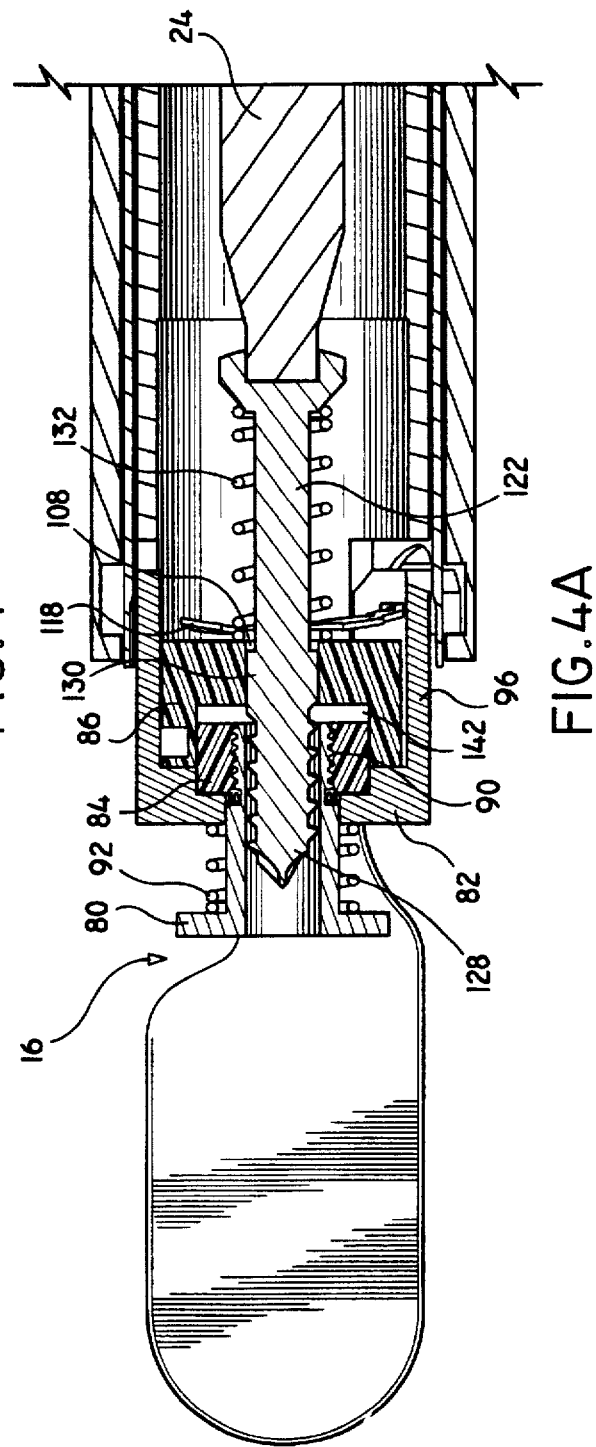

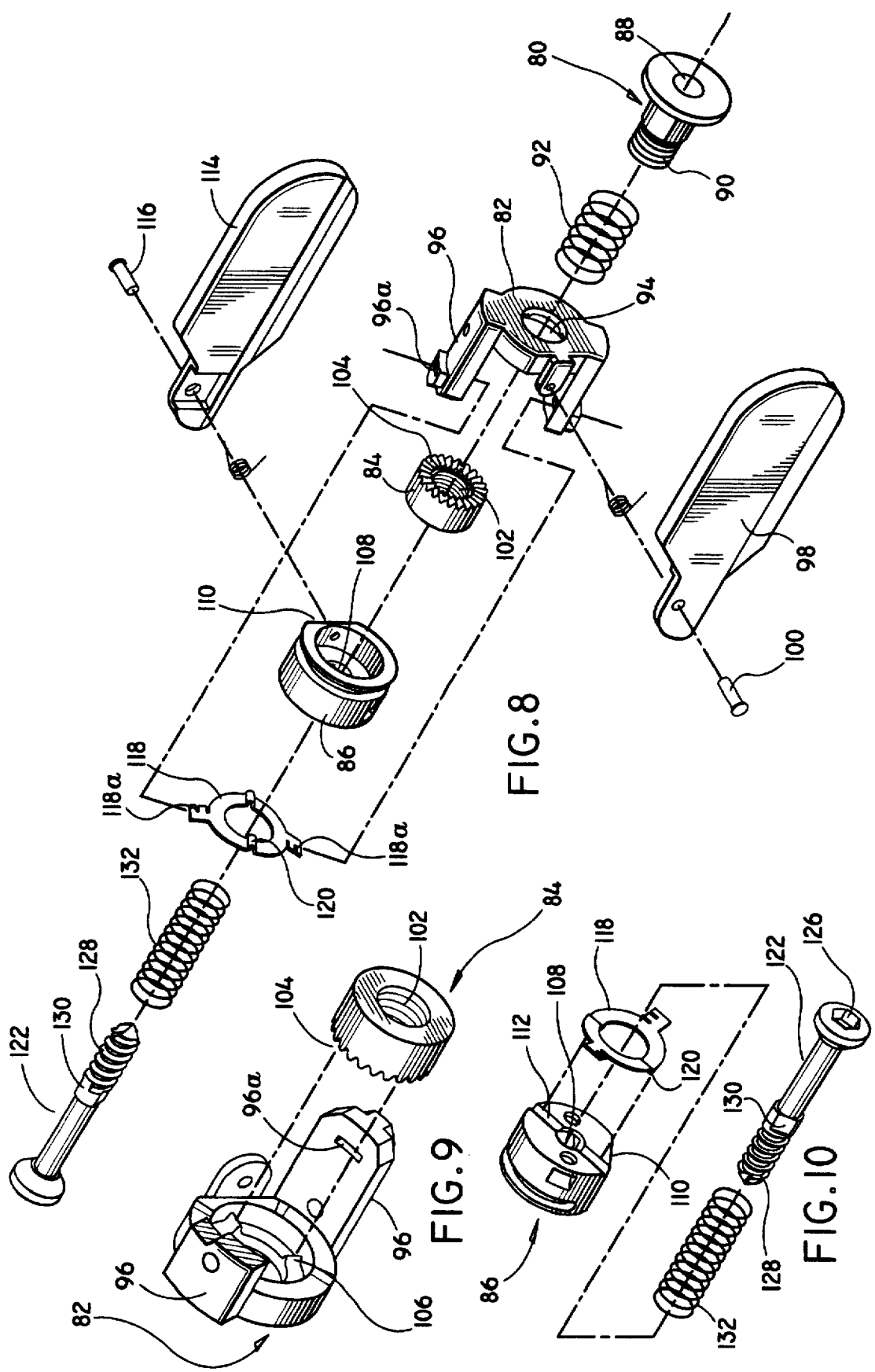

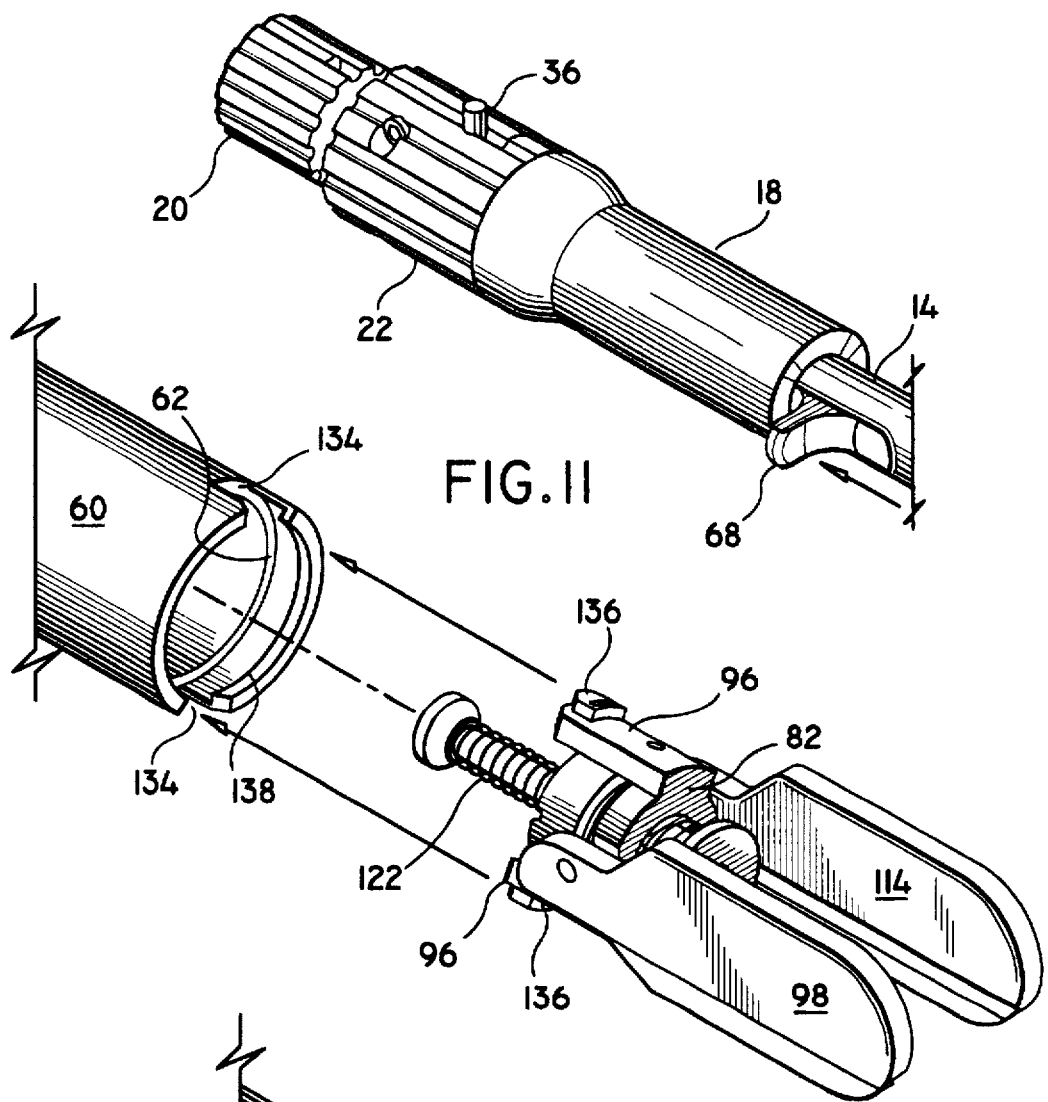
FIG.11
FIG.12
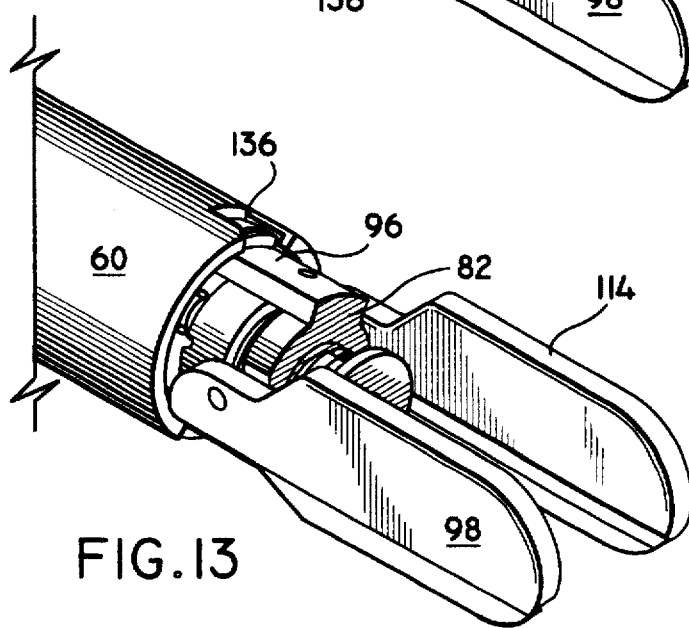
FIG.13

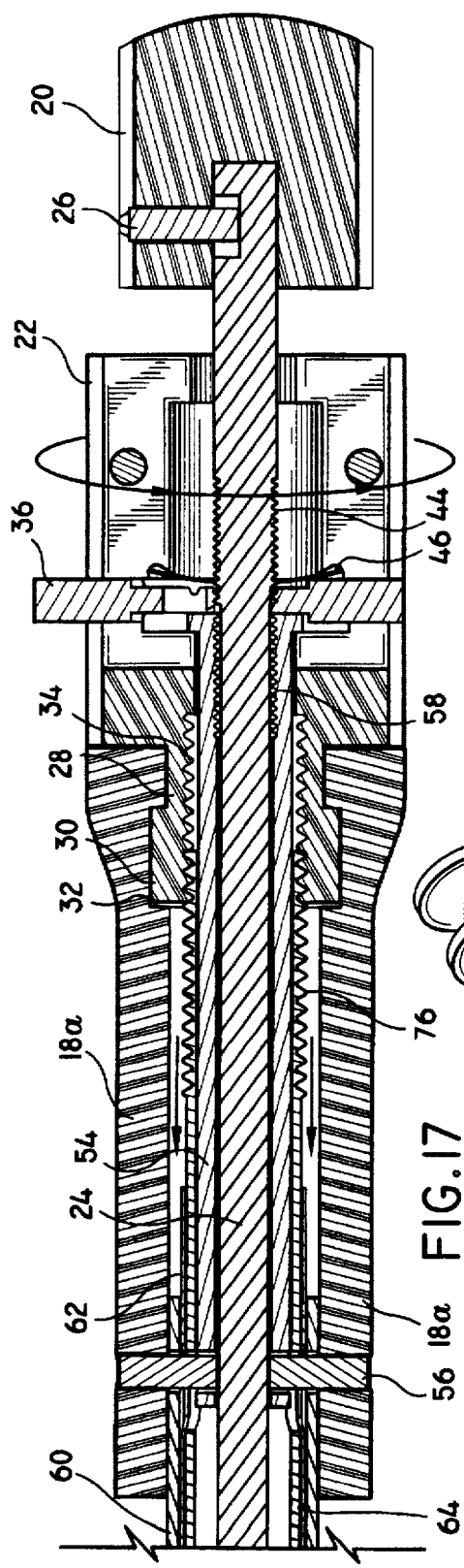
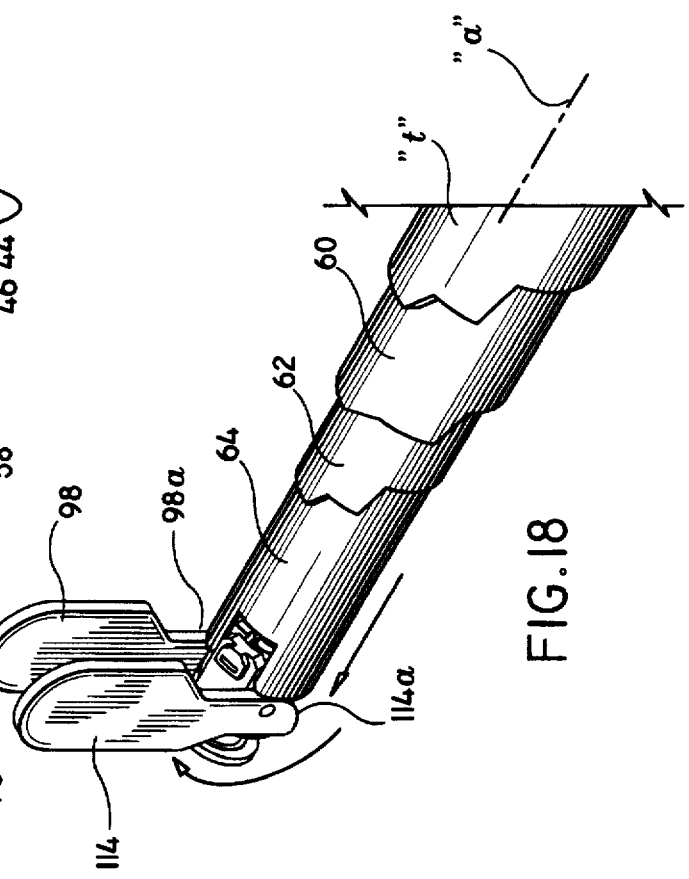
FIG. 17
FIG. 18

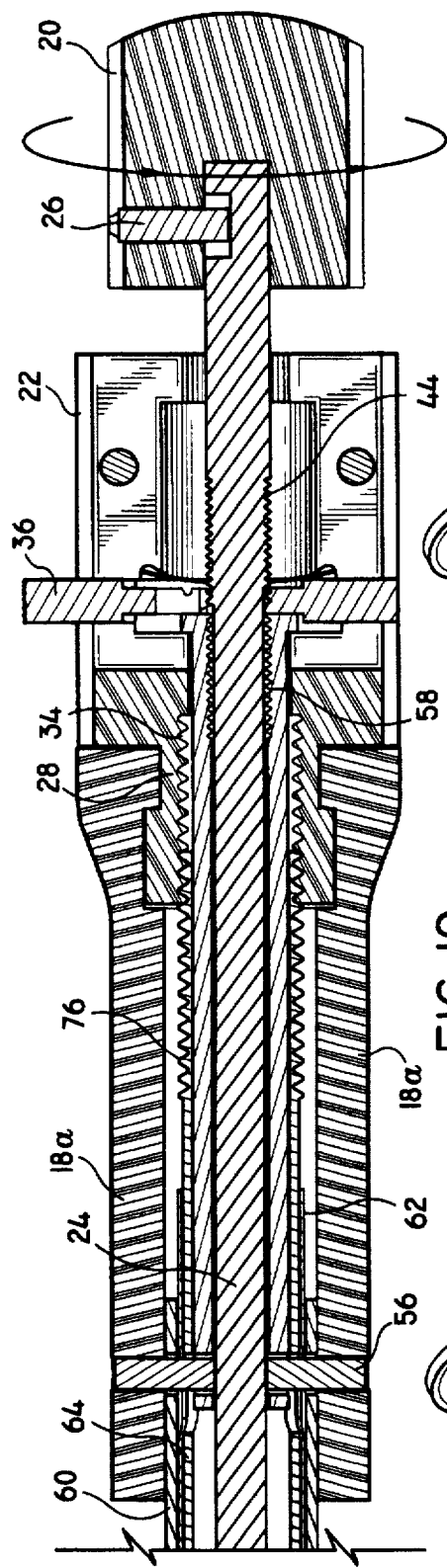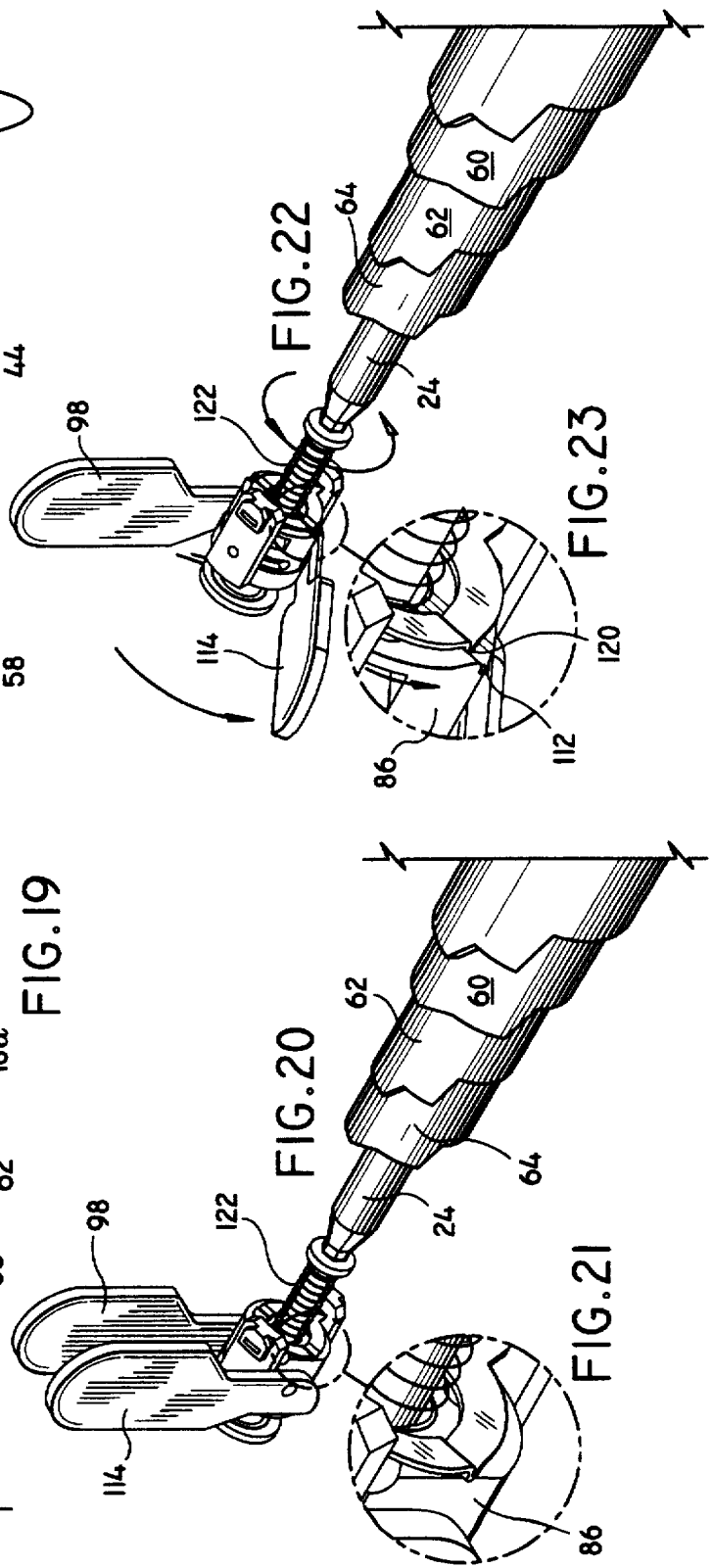

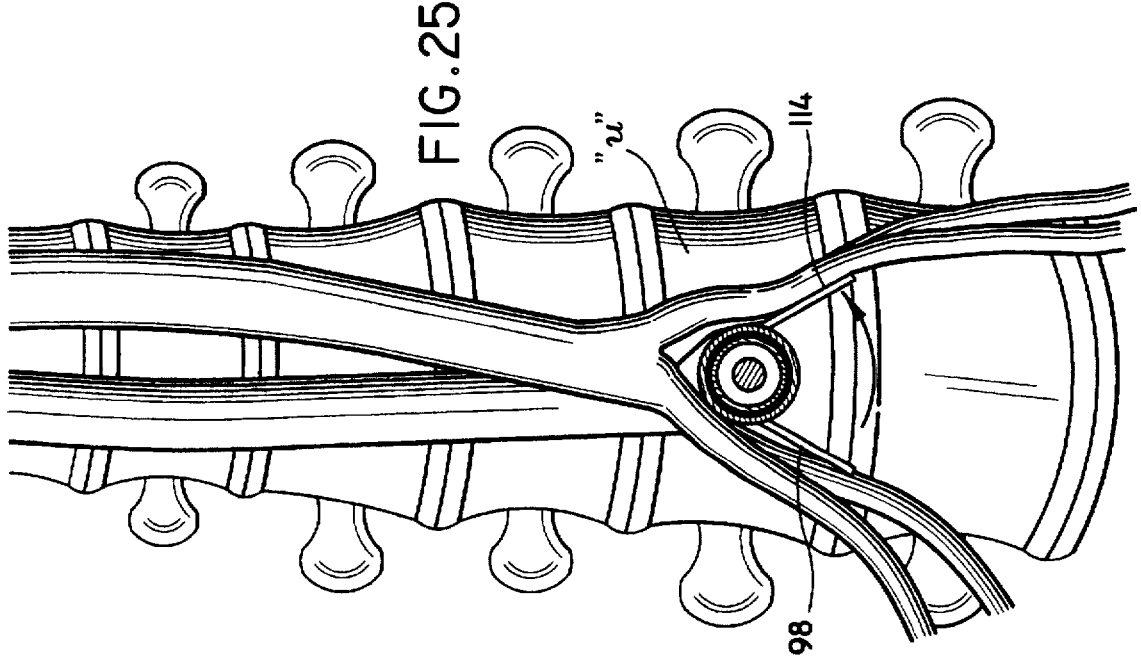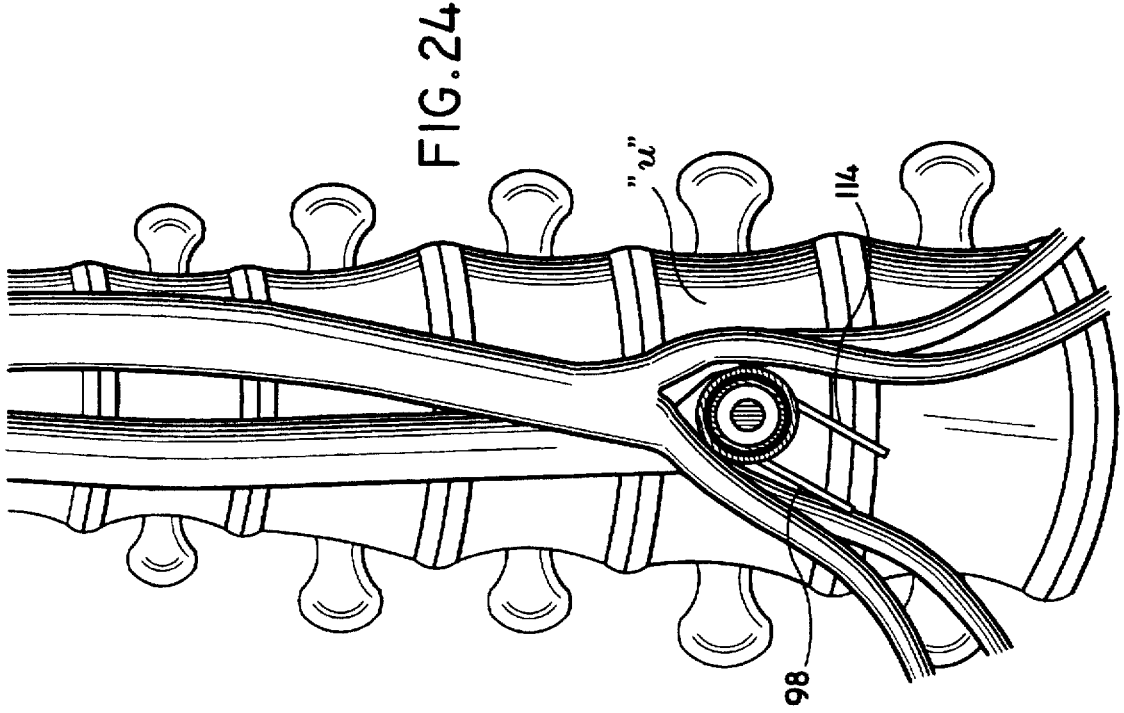

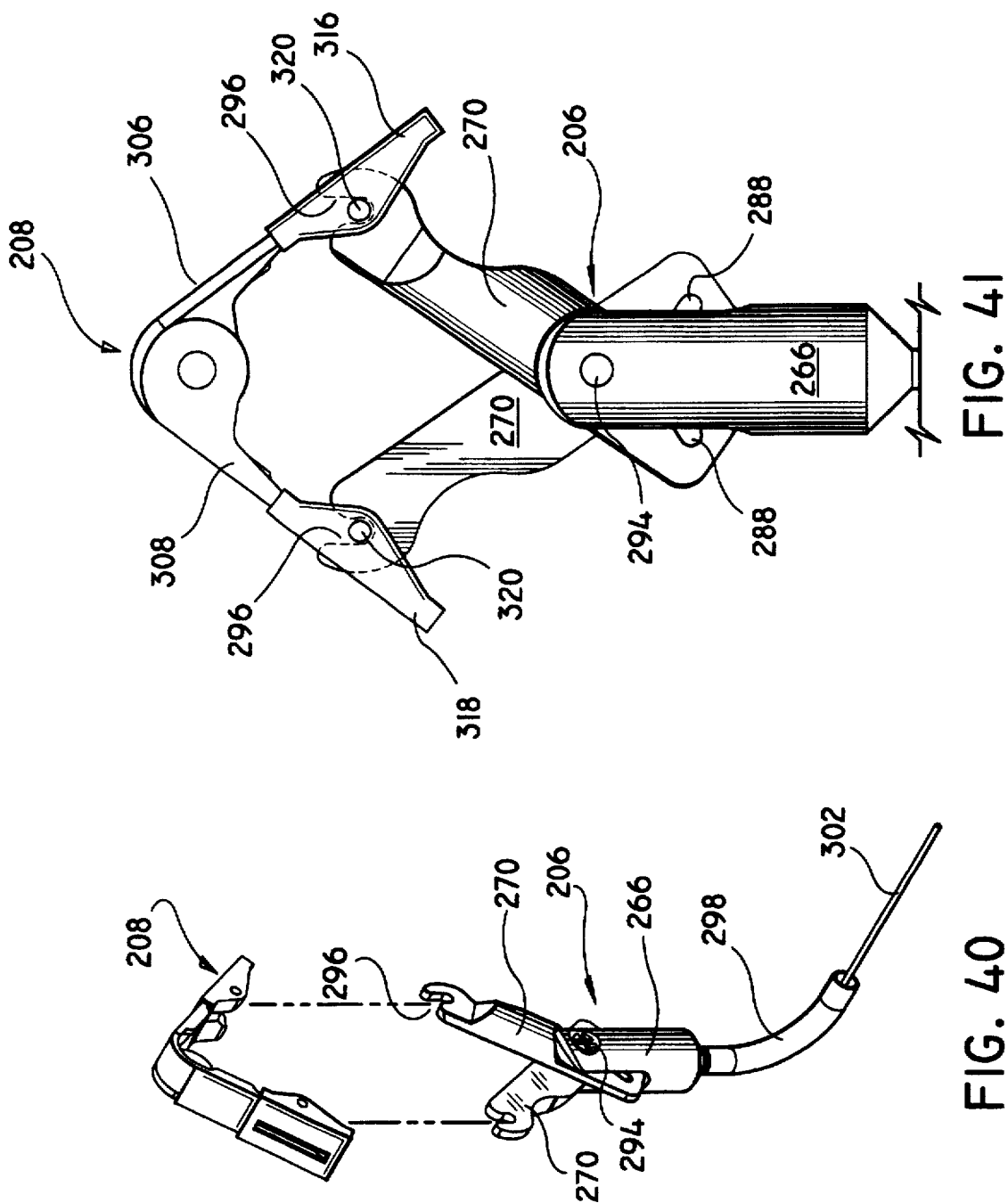

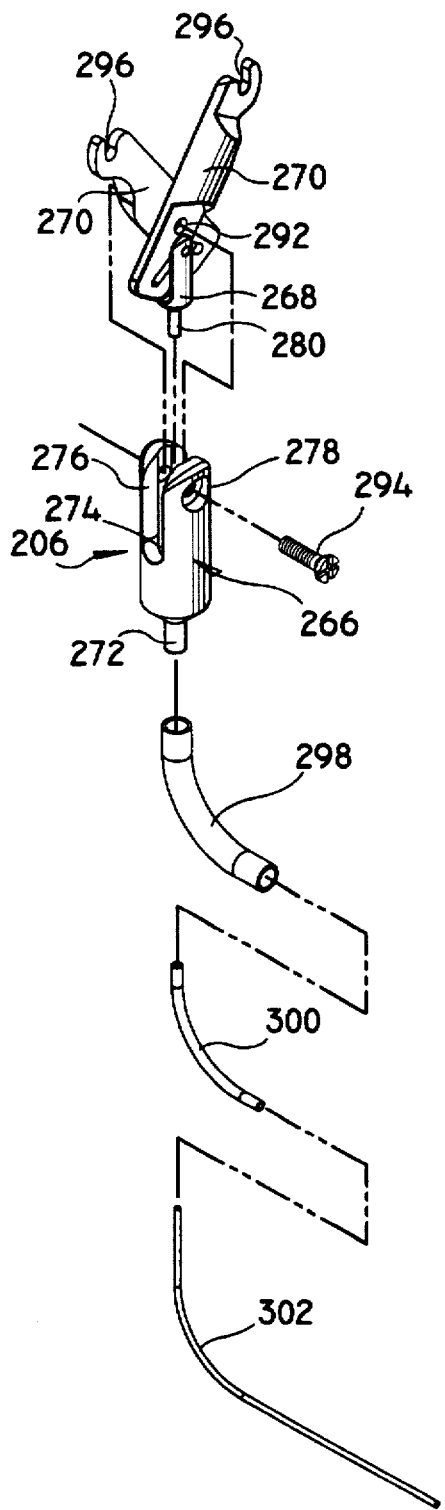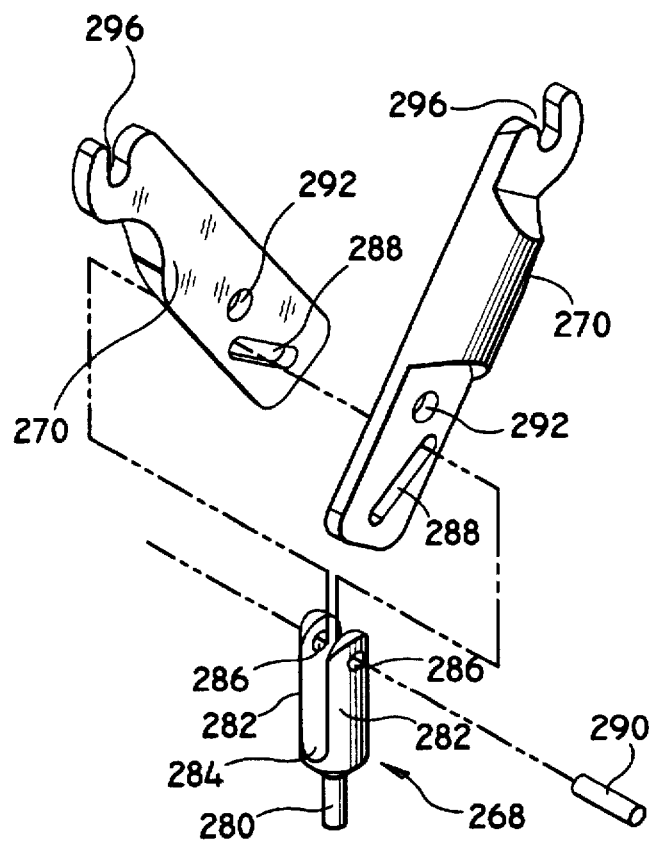
FIG. 43
FIG. 42

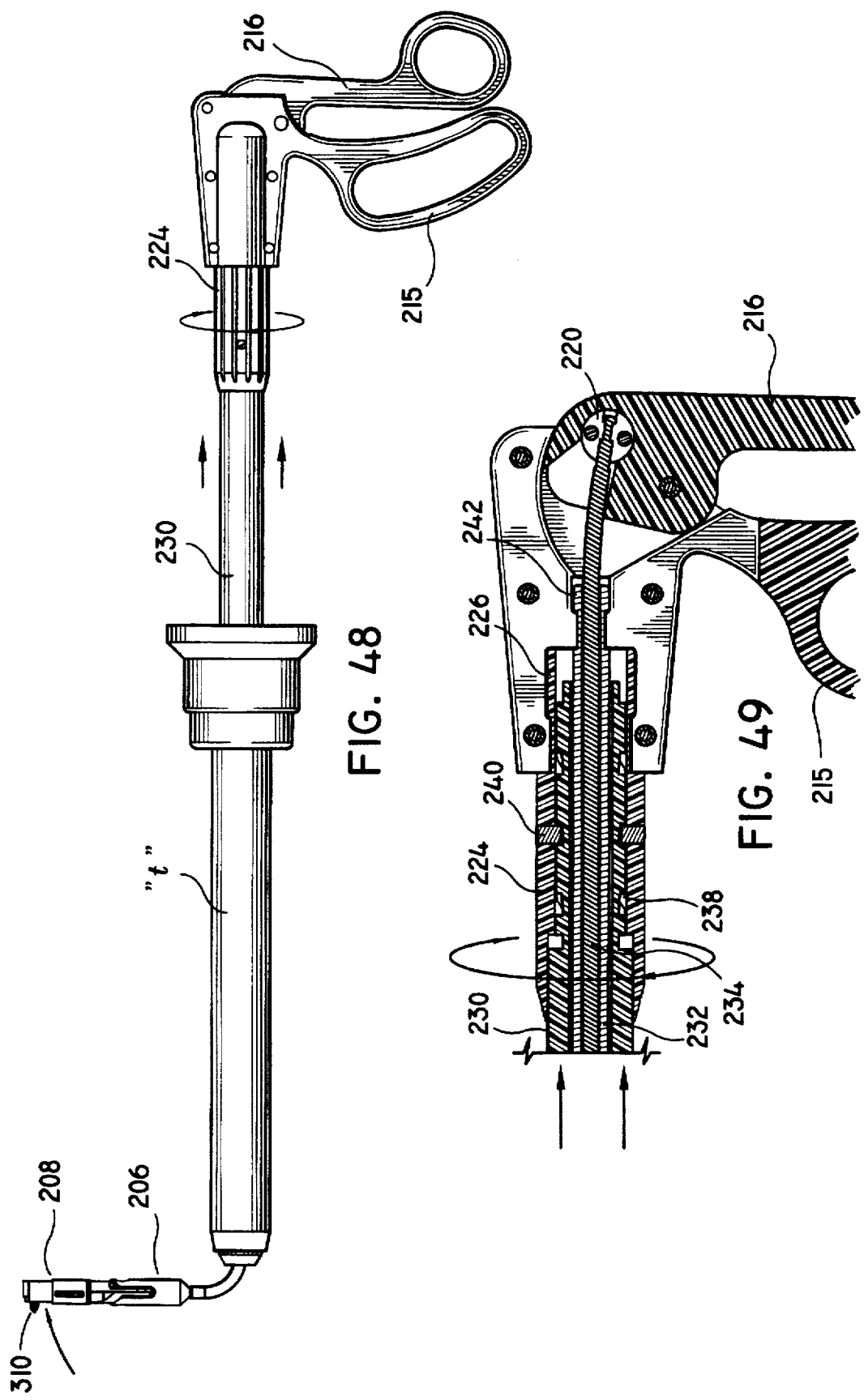

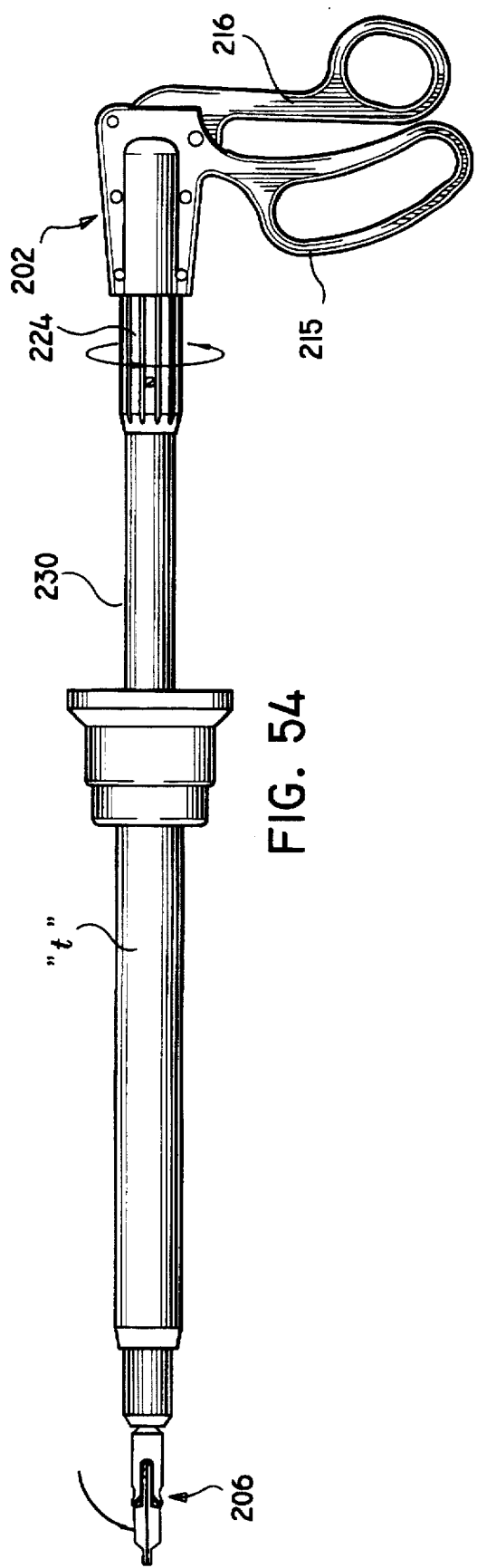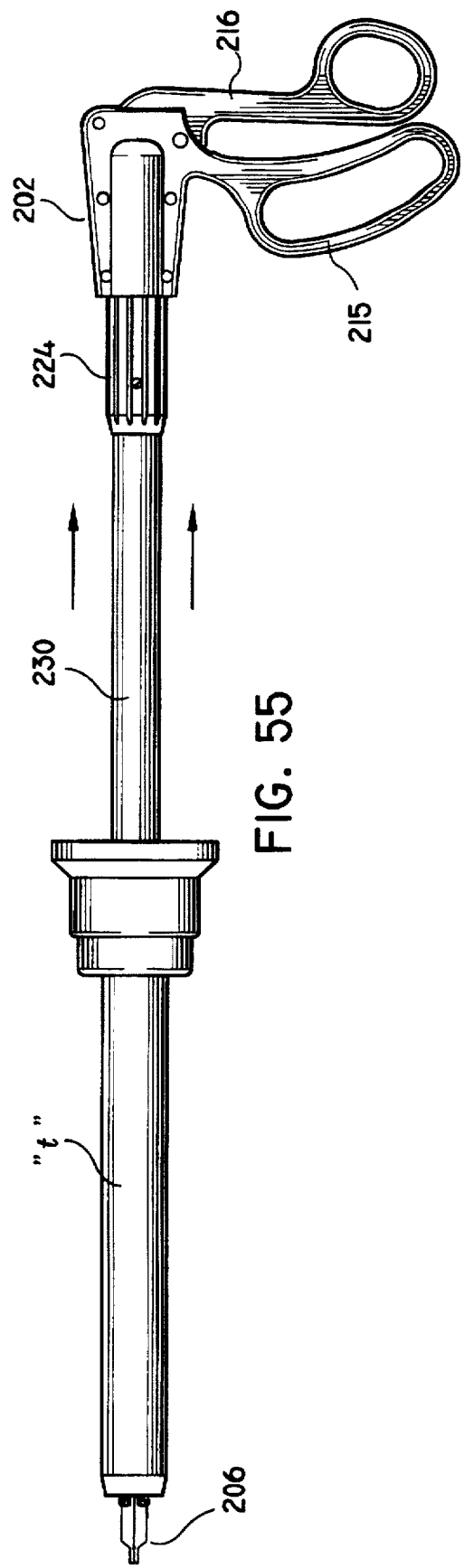

SURGICAL INSTRUMENTS USEFUL FOR SPINAL SURGERY

BACKGROUND

1. Field of the Disclosure

The present disclosure relates to surgical instruments and, more particularly, to endoscopic surgical instruments useful for performing endoscopic discectomy procedures and other minimally invasive spinal procedures.

2. Background of the Related Art

Back pain is a common affliction affecting millions of people. In many instances, back pain is caused by a herniated intervertebral disc. Intervertebral discs are generally cylindrical-shaped structures corresponding to the margins of the adjacent vertebra. An outer ring known as the annulus fibrosus, which is composed of concentric layers of fibrous tissue and fibrocartilage, surrounds a cartilage-like core known as the nucleus pulposus. When an intervertebral disc is herniated, the softer nucleus projects through a torn portion of the annulus, creating a bulge which extends beyond the intervertebral foramen. As a result of the bulging disc, various spinal nerves may be compressed, causing pain or numbness.

Various procedures are used to treat herniated intervertebral discs. In mild disc herniation, pressure on adjacent nerves is lessened through non-surgical techniques. Such techniques include drugs (analgesics, anti-inflammatory drugs, muscle relaxants), physical therapy and rest. If these non-surgical approaches are not successful, surgical intervention is required. Various surgical procedures have been developed to remove at least a portion of the herniated disc. Such procedures include laminotomies, laminectomies, percutaneous discectomy and a newly developed procedure for performing a laparoscopic discectomy.

In laminotomy (also referred to as interlaminar exploration), a posterior approach is used to access the spine through a longitudinal incision. Small amounts of the bony spinal lamina are removed, allowing access to, and removal of, portions of the herniated nucleus pulposus.

Laminectomy is a surgical procedure which, like laminotomy, uses a posterior approach to the herniated disc. In laminectomy, a larger portion of the spinal lamina or laminae are removed to access and remove portions of herniated disc nucleus. Because both laminotomy and laminectomy require removal of bone and retracting of nerve and muscles, hospitalization and recuperation periods are lengthy. Additionally, removal of bone may lead to future spinal instability.

To minimize the need to remove portions of the vertebrae, other approaches to the herniated disc have evolved. In particular, percutaneous discectomy employs a posterolateral approach. Instruments are inserted through a cannula inserted through the patient's side. The disc annulus is pierced and the herniated nucleus is mechanically disintegrated with the pieces being removed through suction. This technique is shown for example in U.S. Pat. Nos. 4,545,374; 5,242,439; and RE 33,258.

In a laparoscopic lumbar discectomy, an anterior approach, i.e., through the abdominal cavity, is utilized to access the spine. In laparoscopic surgical procedures, the abdominal cavity is insufflated with $CO_2$ gas. A surgical trocar which includes a cannula and an obturator positioned within the cannula is applied against the abdominal cavity. The whole assembly is advanced into the abdominal cavity to gain access to the cavity. The obturator is removed to permit the introduction of surgical instruments within the cannula to perform the desired procedure.

In general, each of the above-described discectomy procedures including laparoscopic discectomy, require specialized instruments to perform the various functions associated with the procedures. Such functions may include tissue retraction, calcification removal, tissue sampling and disc removal. With particular emphasis on tissue retraction, a retractor or tissue manipulator is employed to hold or displace tissue to gain access to the underlying and mostly concealed disc material. In the more conventional approaches of discectomy discussed above (i.e., laminotomies, laminectomies), the retractor instrumentation is typically in the form of parallel blade-like structures having two movable blades or paddles. The paddles may includes gripping prongs which pull spinal muscles to one side or hold the muscles in an appropriate place to permit access to the underlying disc. Retractors of this type are disclosed in U.S. Pat. Nos. 4,747,394 to Watanabe and 4,932,395 to Mehdizadek.

Retractors contemplated for endoscopic and/or laparoscopic surgical procedures are known. Conventional laparoscopic retractors are elongated to be inserted through a cannula and are required to be remotely operated. For example, commonly assigned U.S. Pat. No. 5,199,419 to Remiszewski describes a surgical retractor including an elongated housing with a collapsible retractor assembly. The retractor assembly incorporates a plurality of interleaved retractor blades movable to an open fan-like configuration. Another endoscopic retractor is disclosed in U.S. Pat. No. 5,235,966.

With the development of laparoscopic discectomy, however, other designs of endoscopic and/or laparoscopic retractors are needed to accomplish the specialized tasks inherent to the laparoscopic discectomy technique. For example, the anterior approach of laparoscopic discectomy necessitates the selective positioning of various tissue masses disposed adjacent the targeted disc space, including the posterior abdominal lining, a neighboring spinal or lumbar muscle tissue, lumbar and sacral nerve tissue and major blood vessels such as the inferior vena cava and the aorta which are positioned on the anterior side of the spinal column.

Known hand held laparoscopic retractors are not particularly well suited to perform such retracting functions required during a laparoscopic spinal procedure. The tissue retracting structure of these known laparoscopic retractors is relatively oversized and would be difficult to manipulate about the delicate spinal tissue. Furthermore, known laparoscopic retractors lack a self-retaining feature, i.e., these retractors require the surgeon to continuously hold the instrument in the desired position within the operative site during the procedure, thereby precluding the surgeon from performing other functions. Moreover, the presence of the retractor in the spinal area would occupy a significant amount of space in a site which is already restricted.

SUMMARY

Accordingly, the present disclosure is directed to a surgical retractor contemplated for use in laparoscopic discectomy procedures. The retractor incorporates a retractor unit which is releasably mounted to the instrument and is capable of being deployed and mounted directly to bone, e.g., the vertebral column. Once deployed, the retractor unit remains within the operating area until the surgery is completed. The retractor unit is relatively small in dimension, but, is strategically configured to effectively retract spinal tissue including spinalis muscular tissue, the posterior lining and blood vessels, etc . . . , thus, providing enhanced access to the disc area.

In one preferred embodiment, the apparatus includes an elongated portion defining a generally longitudinal axis and having proximal and distal ends, first and second retractor members disposed at the distal end portion of the elongated portion for engaging and spreading tissue, an articulating mechanism operatively connected to the retractor members for selectively articulating the two retractor members and an actuator mechanism operatively connected to the retractor members for causing relative movement between the two retractor members. The retractor members are preferably releasably mounted to the distal end of the elongated portion. A release mechanism for releasing the retractor members from the distal end of the elongated portion is also provided.

The apparatus further includes a tissue penetrating member associated with the retractor members and mounted for movement to facilitate mounting of the retractor members to tissue. The tissue penetrating member is mounted to the distal end of the elongated portion and is movable between a non-deployed position and a deployed position. A deployment mechanism for moving the tissue penetrating member to the deployed position is also provided.

In one alternative embodiment, the retractor members are connected to the distal end of the elongated portion by a connector member. The connector member includes a memory material which is movable between a stressed condition and an unstressed condition. In the unstressed condition of the connector member, the connector member is curved thereby positioning the retractor members in articulated relation with respect to the longitudinal axis. A manually movable member is operatively engageable with the connecting member and is movable to move the connecting member between the stressed and unstressed condition.

In another preferred embodiment, the surgical apparatus includes a handle portion dimensioned to be grasped by the hands of a user, an elongated portion connected to the handle portion and extending distally therefrom and having proximal and distal end portions, at least two retractor blades mounted to the distal end portion of the elongated portion and being adapted for relative movement, a tissue penetrating member operatively associated with the retractor blades and movable to a deployed position to engage tissue and a release mechanism actuable to release the retractor blades and the tissue penetrating member from the distal end portion wherein the tissue penetrating member mounts the retractor blades to the tissue. An actuator member is preferably mounted to the handle portion and operatively engageable with the retractor blades and the tissue penetrating member. In a first mode of operation of the actuator member, movement of the actuator member causes relative movement of the two retractor blades. In a second mode of operation of the actuator member, movement of the actuator member causes movement of the tissue penetrating member to a deployed position. A control member is movable to selectively move the actuator member between the first and second modes of operation.

The retractor blades may also be supported for articulating movement at the distal end portion of the elongated portion through a range of movement from about 0° to about 90° relative to the longitudinal axis. A manually movable member is mounted to the handle portion and is adapted to provide the articulating movement of the retractor blades. A release member may be operatively connected to the retractor blades and the tissue penetrating member. The release member is movable to release the retractor blades and the tissue penetrating member from the distal end portion of the elongated portion.

A method for facilitating the retracting of tissue during a surgical procedure is also disclosed. The method includes the steps of accessing the targeted tissue area, positioning a surgical instrument adjacent the tissue area having an elongated portion, a retractor mechanism with at least two retractor blades releasably mounted to the elongated portion, and a tissue penetrating member associated with the retractor blades, actuating the retractor mechanism to cause relative movement of the retractor blades such that the retractor blades engage and retract tissue to enhance access to a desired tissue area, mounting the tissue penetrating member associated with the retractor blades within tissue, releasing the retractor blades from the elongated portion of the surgical instrument whereby the retractor blades are retained within the tissue by the tissue penetrating member, and performing a surgical procedure adjacent the retracted tissue. A preferred surgical procedure performed in accordance with the method is a laparoscopic discectomy.

BRIEF DESCRIPTION OF THE DRAWINGS

Preferred embodiment(s) of the present disclosure are described herein with reference to the drawings wherein:

FIG. 2A is an isolated perspective view of the distal end portion of the control rod of the elongated portion;

FIG. 4 is a cross-sectional view taken along the lines 4—4 of FIG. 3;

FIG. 4A is a cross-sectional view taken along the lines 4A—4A of FIG. 3;

FIG. 8 is an exploded perspective view with parts separated of the retractor member;

FIG. 9 is an exploded perspective view of the retractor base and toothed collar of the retractor member of FIG. 8;

FIG. 10 is an exploded perspective view of the blade mounting collar and the tissue penetrating member of the retractor member of FIG. 8;

FIGS. 11–16 are views depicting the preferred mounting arrangement for releasably mounting the retractor member to the elongated portion;

FIG. 17 is a side cross-sectional view similar to the view of FIG. 4 illustrating rotation of the articulating knob to cause articulation of the retractor blades of the retractor member;

FIG. 18 is a perspective view of the distal end portion of the elongated portion illustrating advancing movement of the camming sleeve to articulate the retractor blades;

FIG. 19 is a side cross-sectional view similar to the view of FIG. 17 illustrating rotation of the control knob to cause relative movement of the retractor blades;

FIG. 20 is a perspective view of the distal end portion of the elongated portion with portions cut away illustrating the relationship of the control rod, blade mounting collar and tissue penetrating member of the retractor member;

FIG. 21 is an isolated view depicting the relationship of the locking clip and blade mounting collar of the retractor member;

FIG. 22 is a view similar to the view of FIG. 20 illustrating movement of the retractor blades upon rotation of the control knob in the direction depicted in FIG. 19;

FIG. 23 is a view similar to the view of FIG. 21 illustrating the locking clip securely engaging the blade mounting collar to secure the retractor blades in the fully deployed position;

FIG. 24 is a view of the spinal column illustrating the retractor member in a first closed position and disposed adjacent the inferior vena cava and aorta;

FIG. 25 is a view similar to the view of FIG. 24 illustrating the retractor blades in a second open position retracting the vessels of the vena cava and the aorta;

FIG. 40 is a perspective view of the distal deployment mechanism of the instrument and the associated retractor with the retractor disengaged;

FIG. 41 is a plan view of the deployment mechanism and mounted retractor;

FIG. 42 is a perspective view with parts separated illustrating the shape memory tube and main yoke and mounting members of the deployment mechanism;

FIG. 43 is a perspective view with parts separated illustrating the relationship of the minor yoke and mounting members of the deployment mechanism;

FIG. 48 is a view similar to the view of FIG. 47 illustrating rotation of the articulating knob and corresponding articulating movement of the deployment mechanism and retractor;

FIG. 49 is a side cross-sectional view of the handle illustrating the proximal motion of the outer sleeve when the articulating knob is rotated;

FIG. 54 is a side plan view of the instrument with the outer sleeve advanced to straighten the outer tube; and FIG. 55 is a view illustrating removal of the instrument from the trocar.

DETAILED DESCRIPTION OF THE PREFERRED EMBODIMENT(S)

Figure 1:
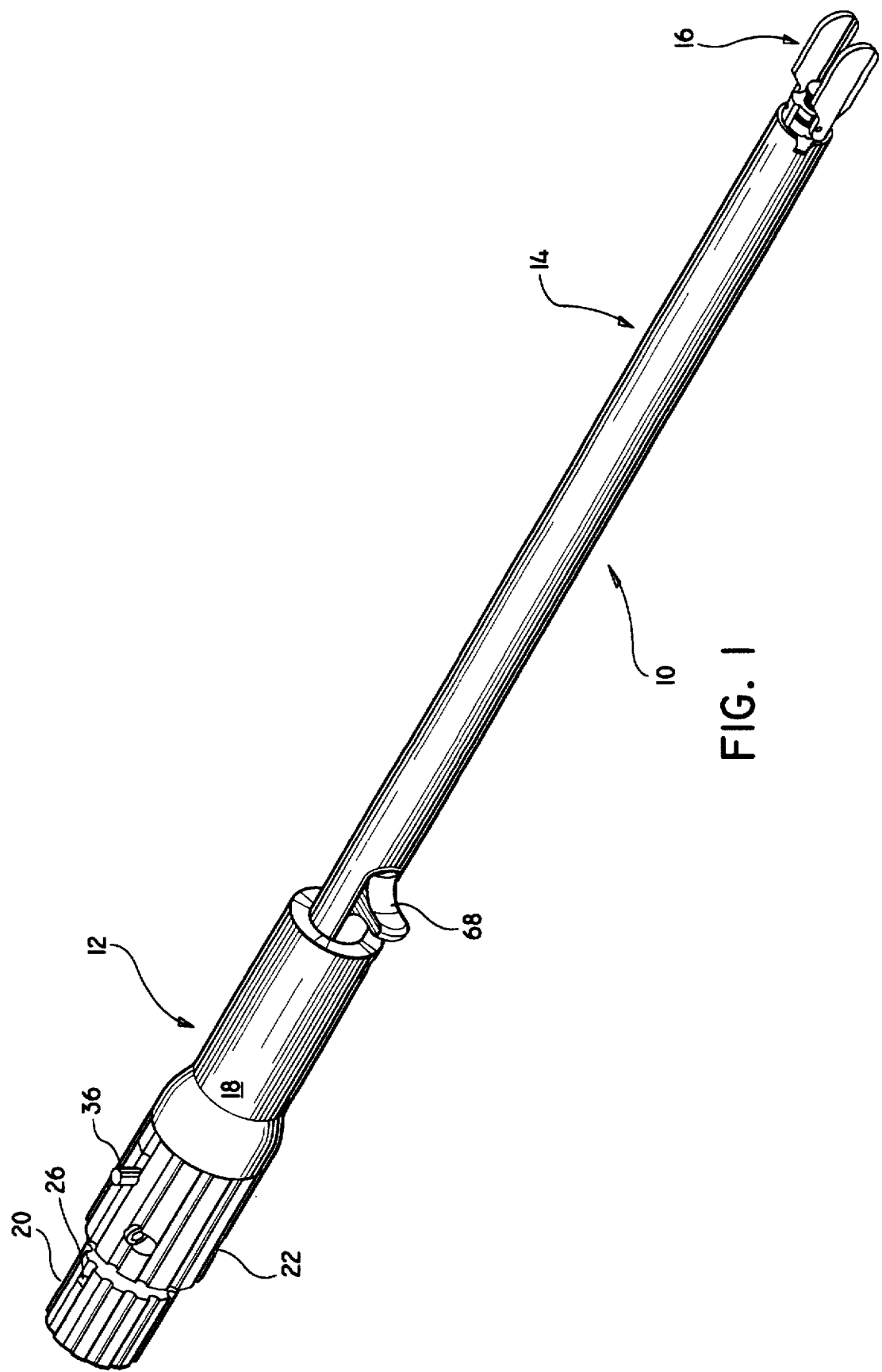
FIG. 1 is a perspective view of a first embodiment of the endoscopic surgical retractor instrument in accordance with the principles of the present disclosure.

Referring now in detail to the drawings in which like reference numerals identify similar or like elements throughout the several views, FIG. 1 illustrates in perspective view, the surgical instrument in accordance with the principles of the present disclosure. Instrument 10 is intended to retract tissue during a surgical procedure and has particular application in retracting spinal tissue, spinalis muscles and blood vessels during an endoscopic discectomy procedure. Other uses of instrument 10 are envisioned as well.

Instrument 10 includes handle portion 12, elongated or endoscopic portion 14 connected to the handle portion 12 and extending distally therefrom, and a retractor 16 which is releasably mounted to the distal end of the elongated portion 14. Generally, handle portion 12 controls movement of retractor 16 such as deployment, articulation and release of the retractor 16. Handle portion 12 also deploys a tissue penetrating member or bone screw associated with retractor 16, which assists in affixing the retractor 16 to a desired tissue, e.g., the vertebral column, as will be discussed.

Figure 2:
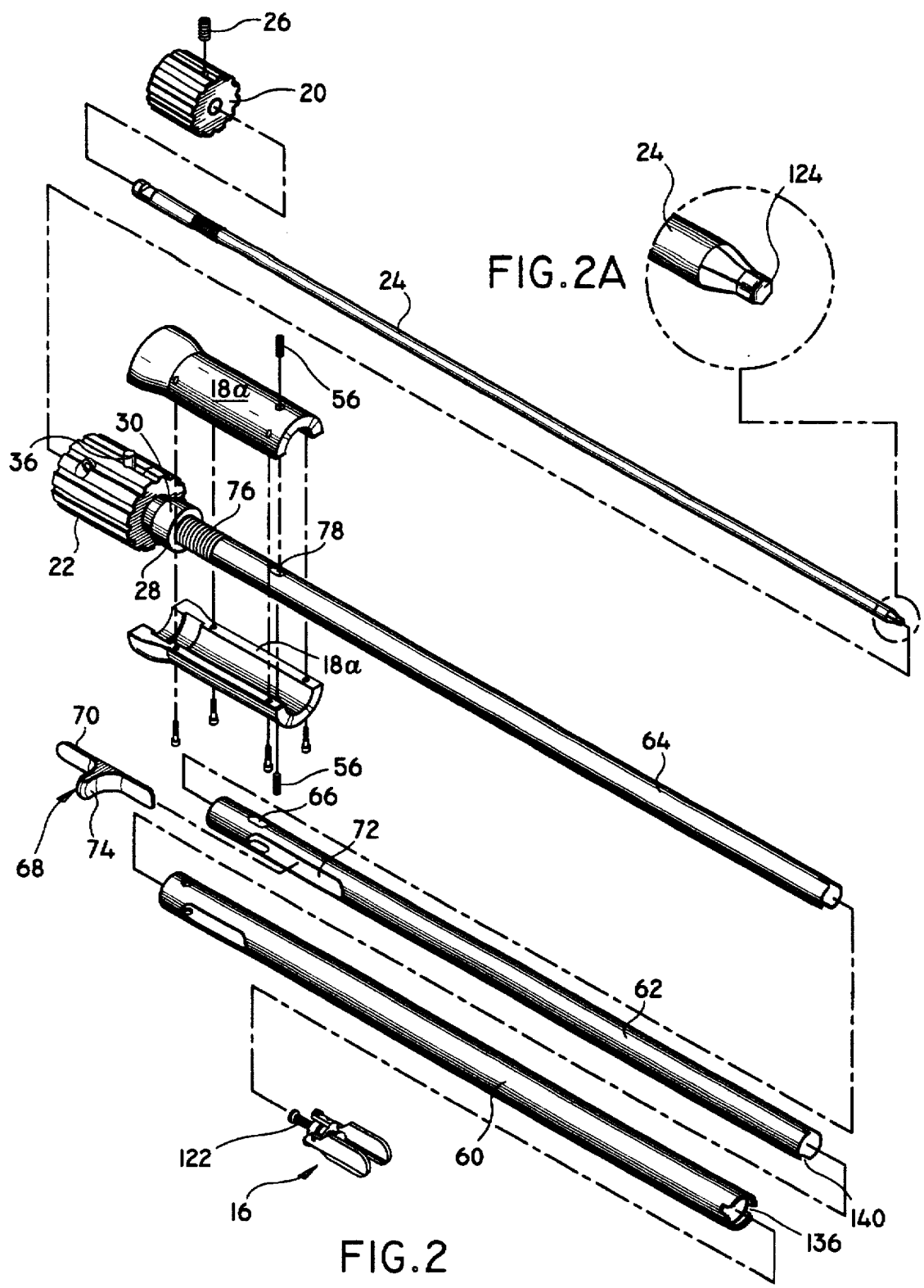
FIG. 2 is a perspective view with parts separated of the instrument of FIG. 1 illustrating the handle portion and the elongated portion.
Figure 3:
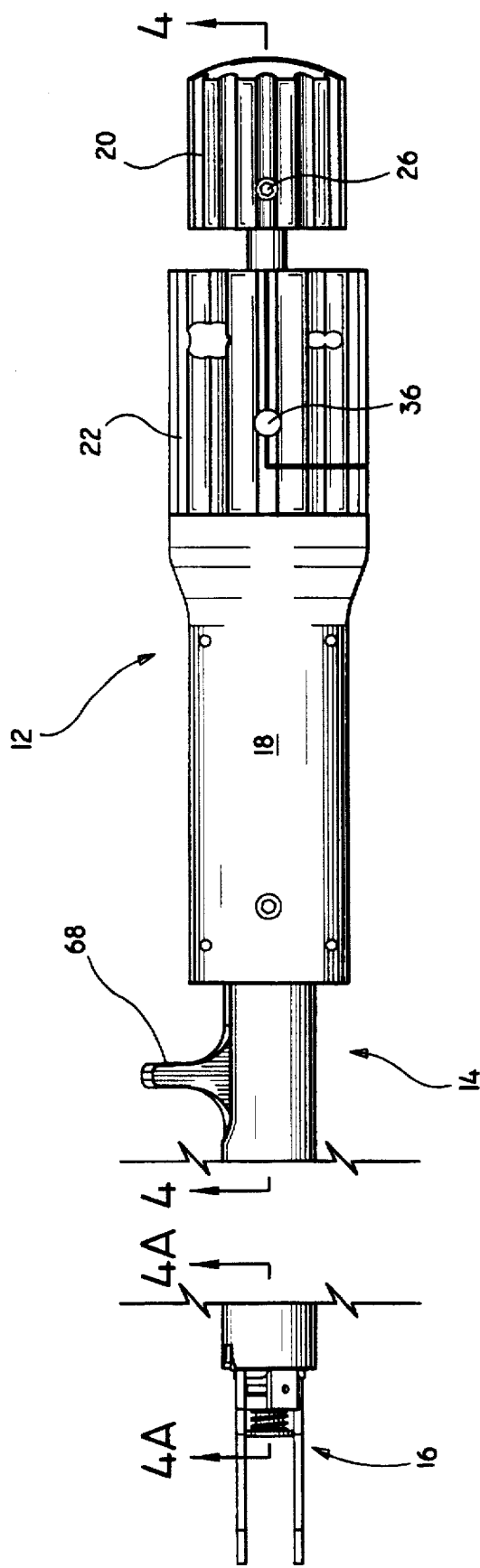
FIG. 3 is a side plan view of the instrument.
Figure 5:
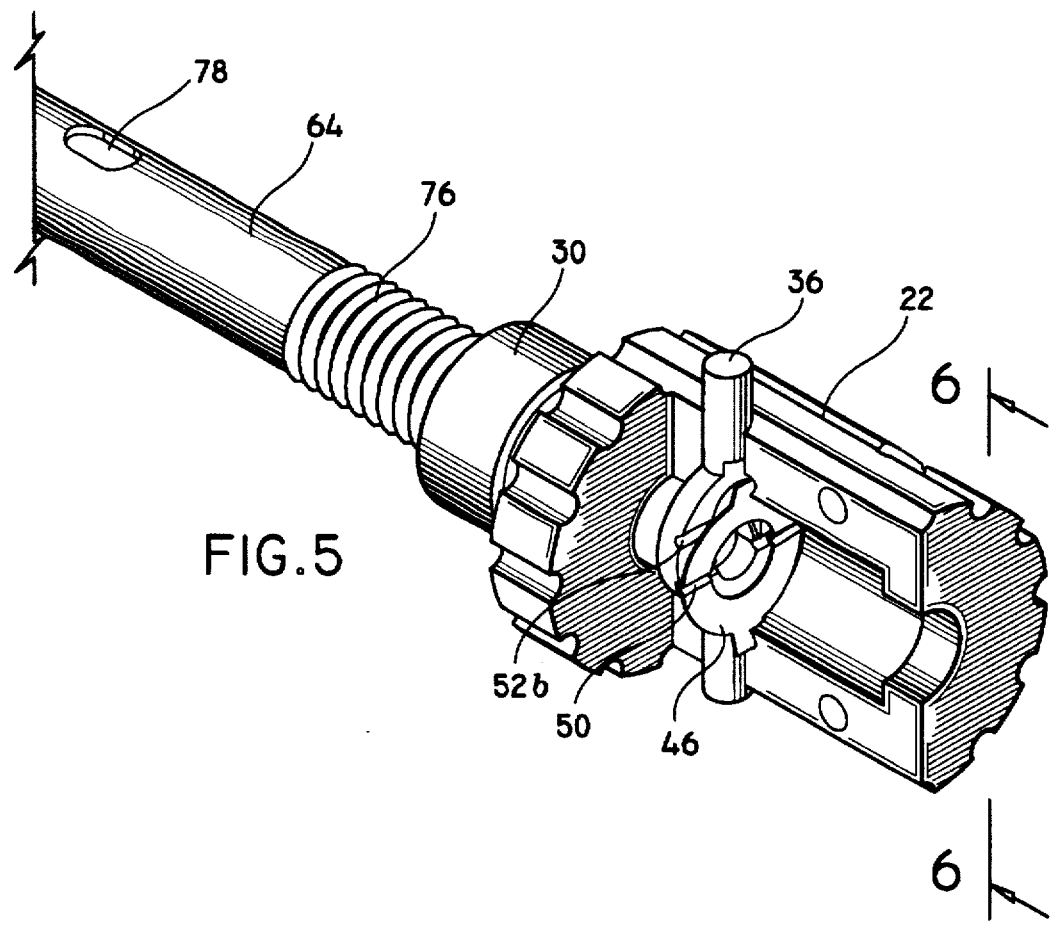
FIG. 5 is a perspective view of the articulating knob of the handle portion with a portion of the knob removed to illustrate the control button for selectively controlling the functioning of the instrument.
Figure 6:
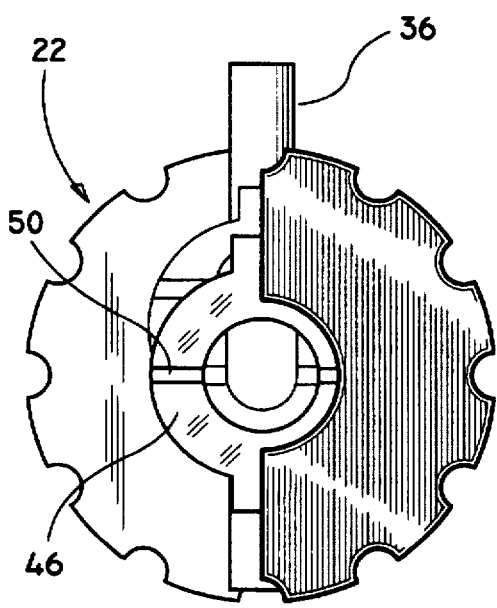
FIG. 6 is a cross-sectional view taken along the lines 6—6 of FIG. 5.

Referring now to FIGS. 2–4, in conjunction with FIG. 1, handle portion 12 includes a housing 18 having half sections 18a connected to each other along their peripheries via screws, pins, adhesives or the like, dual functioning rotatable control knob 20 and a rotatable articulating knob 22 disposed intermediate the control knob 20 and the housing 18. Control knob 20 is fixedly connected to control rod 24 through mounting pins 26 and provides dual functions to instrument 10. In particular, in a first mode of operation of control knob 20, rotation of the knob 20 causes corresponding rotation of control rod 24 thereby causing retracting movement, i.e., opening and closing, of retractor 16. In a second mode of operation of control knob 20, rotation of the knob 20 serves in deploying the tissue penetrating member associated with the retractor 16. The outer surface of control knob 20 is scalloped to enhance user engagement. The operation of control knob 20 will be discussed in greater detail hereinbelow.

Articulating knob 22 has a flange 28 mounted to its forward end. Flange 28 defines a distal collar portion 30 which is received within a correspondingly dimensioned internal recess 32 formed within housing 18 to rotatably mount articulating knob 22 to the housing 18. Flange 28 defines an internal threaded bore 34 as shown. Articulating knob 22 also has an outer scalloped surface to enhance gripping engagement.

Referring now to FIGS. 4–7, handle 12 further includes control button 36 which serves in switching the functioning of control knob 20 between its first and second modes of operation. Button 36 is mounted to articulating knob 22 and is reciprocally movable in a vertical or transverse direction between a first or upper position shown in FIGS. 4–6 and a second or lower position. The first position of control button 36 corresponds to the first mode of operation of control knob 20 (i.e., controlling relative movement of the retractor blades of retractor 16) while the second or downward position of the button 36 corresponds to the second mode of operation of the knob 20 (i.e., controlling deployment of the tissue penetrating member).

Figure 7:
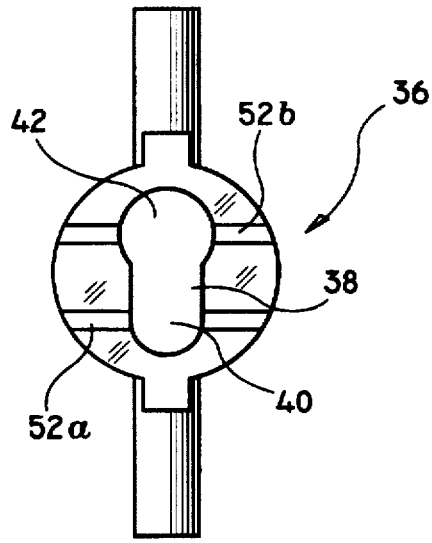
FIG. 7 is an axial plan view of the control button depicted in FIG. 5.

As best depicted in FIG. 7, control button 36 defines a keyway-shaped slot 38 therethrough having first and second openings 40, 42 respectively. First opening 40 defines a cross-sectional dimension which is less than the cross-sectional dimension of second opening 42 as shown. In the first position of button 36, control rod 24 passes through first opening 40 of the button as depicted in FIG. 4. In such position of button 36, control rod 24 is capable of rotating, but, is prevented from advancing distally relative to housing 16 by the engagement of the forward end of threaded portion 44 of control rod 24 with the button portion defining first opening 40. (FIG. 4) In particular, the cross-sectional dimension of threaded portion 44 of control rod 24 is greater than the cross-sectional dimension of first opening 40, thus, precluding control rod 24 from advancing within button 36. When button 36 is in its second downward position, second opening 42 of the button 36 is in alignment with control rod 24 (i.e., control rod 24 passes through second opening 42). The cross-sectional dimension of second opening 42 is greater than the cross-sectional dimension of threaded portion 44, thus, permitting control rod 24 to translate distally through button 36.

Referring again to FIGS. 4–7, a resilient apertured clip 46 is mounted adjacent button 36 within a correspondingly dimensioned and configured inner recess 48 (FIG. 4) defined within articulating knob 22. Resilient clip 46 has a pair of diametrically opposed forwardly projecting tab members 50. Similarly, control button 36 has lower and upper pairs of locking grooves 52a, 52b respectively formed in its proximal face. Locking grooves 52a, 52b receive projecting tabs 50 to secure control button 36 in its first or second position, i.e., in the upper or first position of button 36, the projecting tabs 50 of resilient clip 46 lockingly engage the lower set of locking grooves 52a to releasably retain the button 36 in this position. When control button 36 is in its second or downward position, projecting tabs 50 engage the upper pair of locking grooves 52b to releasably retain the button 36 in its second position.

Referring particularly to FIGS. 4–4A, handle portion 12 further includes translating sleeve 54. Translating sleeve 54 is disposed adjacent button 36 and is fixedly mounted within housing 18 through opposed mounting pins 56. Translating sleeve 54 has an internal threaded portion 58 at its proximal end which is threadably engageable with threaded portion 44 of control rod 24.

The components of handle portion 12 are preferably fabricated from a polymeric material including polycarbonate or a nylon-filled polymeric component for added rigidity. The components of handle portion 12 may also be fabricated from metallic materials including stainless steel, aluminum alloy, etc . . .

Referring now to FIGS. 1, 2, 2A, 4 and 4A, elongated portion 14 of instrument 10 will be discussed. Elongation portion 14 includes a plurality of coaxially mounted tubes or sleeves, particularly, outer sleeve 60, locking sleeve 62 immediately disposed within the outer sleeve 60 and camming sleeve 64 disposed within the locking sleeve 62. Elongated portion 14 also includes the aforementioned control rod 24. Outer sleeve 60 is fixedly mounted to housing 18 through mounting pins 56 as depicted in FIG. 4. Locking sleeve 62 is adapted for reciprocal longitudinal movement within outer sleeve 60 and has a slotted portion 66 which receives mounting pins 56. Slotted portion 66 is elongated as shown (FIG. 2) to permit reciprocal movement of the locking sleeve 62 within a limited range of motion.

A release trigger 68 is disposed adjacent housing 18. Release trigger 68 includes a base 70 which interfits with a correspondingly dimensioned mounting slot 72 defined in locking sleeve 62 to operatively connect the trigger 68 and the locking sleeve 62. (FIG. 2) As a result of this arrangement, axial movement of the trigger 68 causes locking sleeve 62 to translate accordingly. The trigger portion 74 of release trigger 68 extends through an opening in outer sleeve 60 for engagement by the operator. Release trigger 68 functions in releasing retractor 16 from its mounting to elongated portion 14 as will be discussed.

Referring particularly to FIGS. 2, 4 and 4A, camming sleeve 64 includes a proximal threaded portion 76 which threadably engages internal threaded bore 34 of flange 28 which is attached to articulating knob 22. Camming sleeve 64 is mounted for reciprocal longitudinal movement within outer sleeve 60 as effectuated through corresponding rotation of articulating knob 22 and the threaded relationship of flange 28 and camming sleeve 64. Camming sleeve 64 is mounted to housing 16 through mounting pins 56 which are received within slots 78 defined in the camming sleeve 64. Slots 78 are relatively elongated as shown to permit longitudinal movement of camming sleeve 64.

Referring now to FIGS. 8–10, in conjunction with FIG. 1, retractor 16 of instrument 10 will be discussed. Retractor 16 includes, from distal to proximal, locking cap 80, retractor base 82, toothed collar 84 and blade mounting collar 86. Locking cap 80 has an internal bore 88 and a proximal outer threaded portion 90. A coiled spring 92 is mounted about at least the threaded portion 90 of locking cap 80 and engages respective end surfaces of retractor base 82 and the cap 80. Retractor base 82 has an aperture 94 which receives a portion of locking cap 80 and a pair of diametrically opposed mounting wings 96 extending in a general longitudinal direction. A first retractor blade 98 is mounted to retractor base 82 through mounting pin 100.

Toothed collar 84 includes an internal threaded bore 102 which is threadably engaged by the threaded portion 90 of locking cap 80. A plurality of external teeth 104 are defined on the distal end face of toothed collar 84. Teeth 104 engage corresponding locking projections 106 (FIG. 9) disposed on the proximal face of retractor base 92. The significance of teeth 104 of toothed collar 84 and locking projections 106 of retractor base 92 will be discussed.

Blade mounting collar 86 includes bore 108 and a generally planar surface 110 which is disposed on the exterior surface of the collar 86. Bore 108 is preferably generally D-shaped in cross section. Mounting collar 86 further includes a diametrical groove 112 (FIG. 10) on its proximal surface. A second retractor blade 114 is mounted to planar surface 110 of mounting collar 86 through mounting pin 116. Blade mounting collar 86 has a resilient clip 118 disposed on its proximal side. Resilient clip 118 is mounted to retractor base 82 by the corresponding reception of opposed clip tab portions 118a (FIG. 8) within corresponding mounting apertures 96a defined in mounting wings 96. Resilient clip 118 has distally facing projections 120 which are receivable within groove 112 of mounting collar 86 to lock the mounting collar 86 at a predetermined rotational orientation with respect to retractor base 82 as will be discussed.

Referring now to FIGS. 4A and 8–10, retractor 16 further includes a tissue penetrating member or bone screw 122. Tissue penetrating member 122 is releasably mounted to the distal end portion of control rod 24 by the reception of the hexagonal-shaped distal head 124 of the rod 24 (FIG. 2A) within the correspondingly dimensioned hexagonal shaped recess 126 formed in the proximal face of tissue penetrating member 122 (FIG. 10). In this manner, rotational movement of control rod 24 causes corresponding rotational movement of tissue penetrating member 122. Tissue penetrating member 122 further includes a distal outer threaded portion 128 which facilitates penetration through hard tissue and an intermediate mounting section 130. Mounting section 130 has a D-shaped cross-section corresponding in dimension to the cross-section of bore 108 of blade mounting collar 86. Other shapes of bore 108 and mounting section 130 are envisioned as well. A coil spring 132 is disposed about tissue penetrating member 122 and engages at its distal end mounting collar 86 to normally bias the mounting collar 86 distally.

As best depicted in the cross-sectional view of FIG. 4A, in the fully assembled condition of retractor 16, tissue penetrating member 122 passes through the respective bores of resilient clip 118, mounting collar 86, toothed collar 84, retractor base 82 and locking cap 80. Mounting section 130 of tissue penetrating member 122 is disposed within bore 108 of mounting collar 86. Due to the corresponding cross-sectional arrangement of mounting section 130 of tissue penetration member 122 and bore 108 of mounting collar 86, rotational movement of the tissue penetrating member 122 causes corresponding rotational movement of the collar 86 when the instrument is in the condition depicted in FIGS. 4–4A. As further depicted in FIG. 4A, the entire retractor 16 is biased distally by coil spring 132. The locking cap 80 and toothed collar 84 arrangement (as provided through the threaded engagement of threaded portion 90 of locking cap 80 and internal threaded portion 102 of toothed collar 84) is biased distally by coil spring 92. It is to be appreciated that the distal bias of locking cap 80 and toothed collar 84 forces teeth 104 to lockingly engage locking projections 106 of retractor base 92 thereby precluding retractor base 92 from rotating relative to the cap 80 and collar 84. (FIGS. 4A & 9).

Referring now to FIGS. 11–13, the preferred mounting mechanism for releasably mounting retractor 16 to the distal end of elongated portion 14 will be discussed. Prior to mounting retractor 16, release trigger 68 is moved in a proximal direction to the position shown in FIG. 11. This movement causes locking sleeve 62 to move proximally through the interaction of trigger 68 with mounting slot 72 of the locking sleeve 62 (FIG. 2). With locking sleeve 62 in the proximal position shown in FIG. 12, mounting wings 96 of retractor base 82 are then aligned with a pair of diametrically opposed notches 134 defined in the distal end of outer sleeve 60 and the retractor 14 is at least partially positioned within the interior of the outer sleeve 60 as depicted in FIG. 13.

Figure 14:
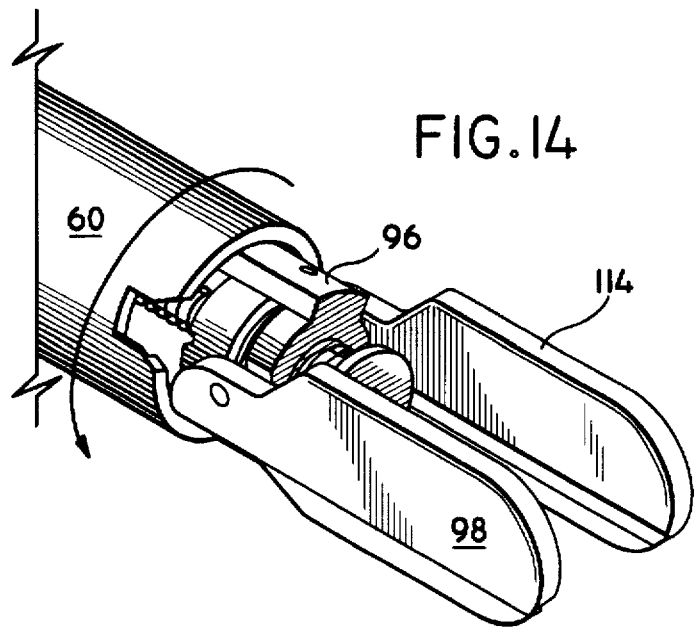
Figure 15:
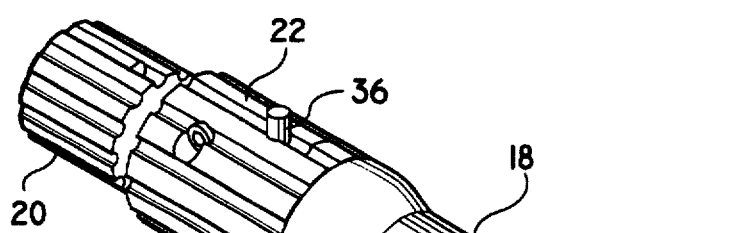
Figure 16:
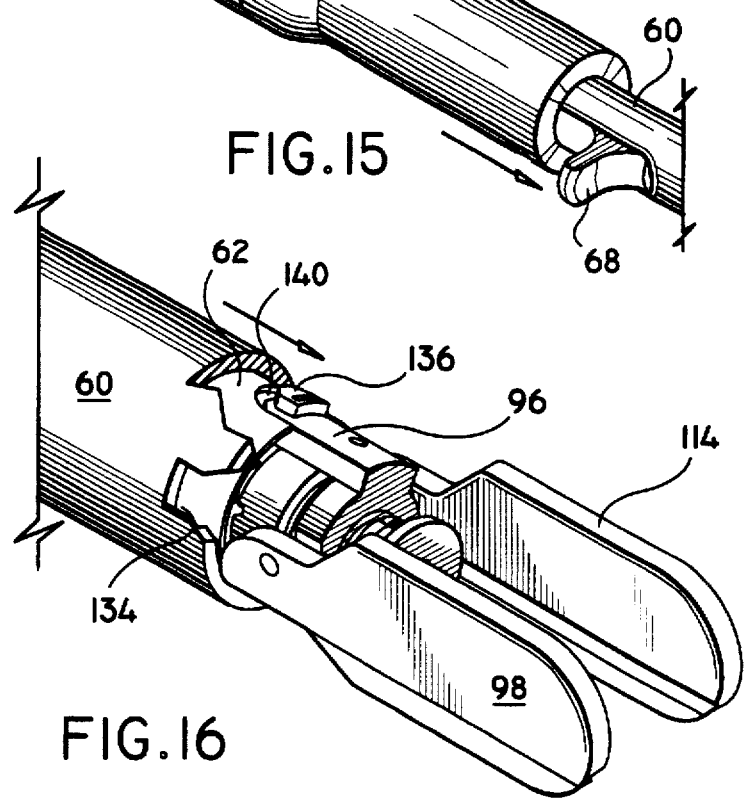
Figure 26:
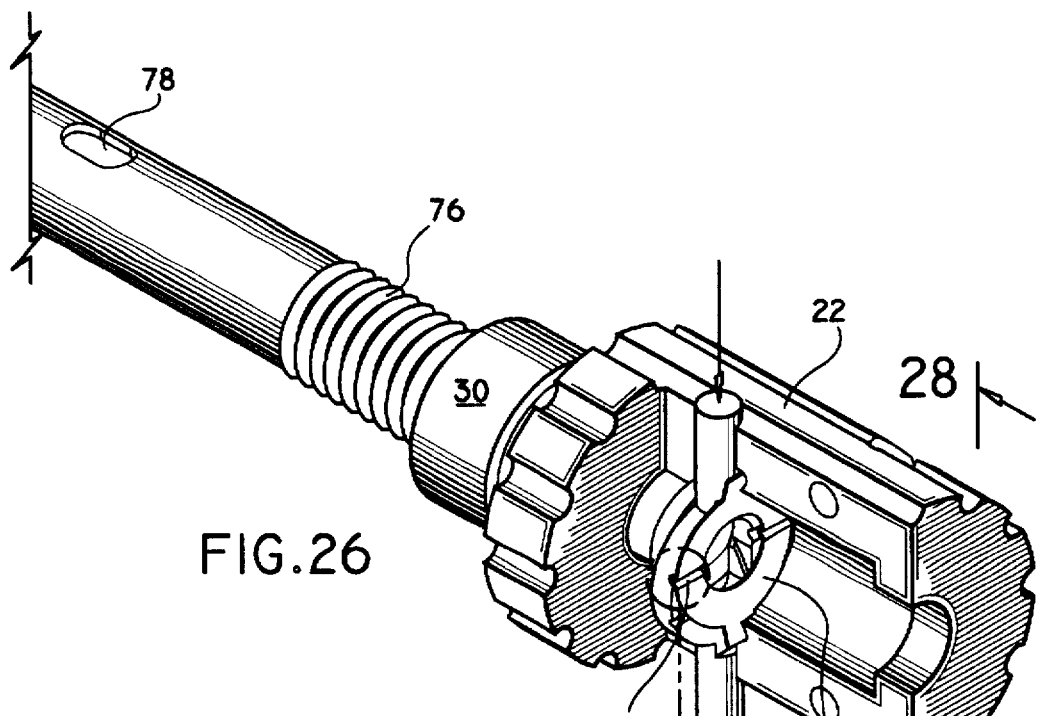
FIG. 26 is a view similar to the view of FIG. 5 illustrating the control button moved to its downward position to switch the operating mode of the instrument.
Figure 27:
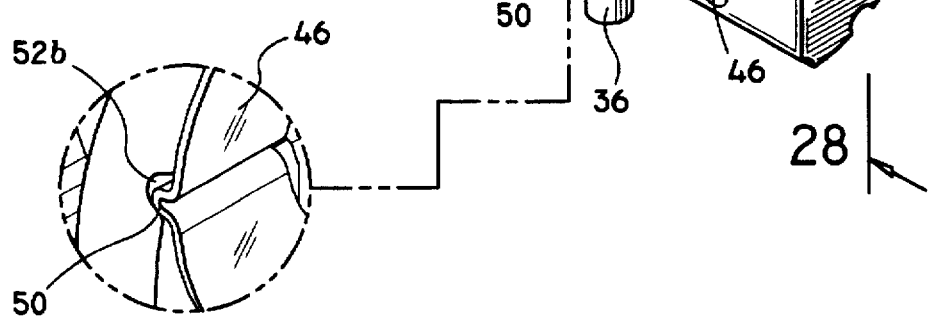
FIG. 27 is an isolated view illustrating the locking clamp securing the control button in its downward position.

With reference now to FIG. 14, instrument 10 is then rotated in the direction indicated by the directional arrow of FIG. 14 while retractor 16 is held stationary. Alternatively, retractor 16 may be rotated while instrument 10 is held stationary. With reference to FIGS. 12 and 14, upon rotation of instrument 10 and outer sleeve 60, mounting heads 136 extending from mounting wings 96 are retained between the distal end of locking sleeve 62 and locking shelf 138 which is disposed at the distal end of outer sleeve 60. With reference now to FIGS. 15–16, release trigger 68 is thereafter distally advanced. Upon advancing movement of locking sleeve 62, distal mounting notches 140 (FIGS. 2 and 16) defined in the distal end of the locking sleeve 62 receive mounting heads 136 of retractor base 82 to engage the heads and thus prevent rotational movement of retractor 16 within outer sleeve 60 thereby retaining the retractor 16 on elongated portion 14.

Operation

The operation of instrument 10 will now be discussed in conjunction with retracting tissue such as the posterior lining, spinalis muscle tissue and/or adjacent blood vessels during an endoscopic discectomy procedure. Instrument 10 in the arrangement of FIG. 1 is positioned within an appropriate trocar sleeve accessing the abdominal cavity. Note that retractor blades 98, 114 are in general parallel alignment with the longitudinal axis of the elongated portion 14 during insertion. The instrument 10 is advanced within the trocar sleeve to its targeted position, e.g., adjacent a disc space. With reference now to FIGS. 17 and 18 (FIG. 18 depicts instrument 10 at least partially positioned in trocar tube "t"), articulating knob 22 is rotated in the direction indicated by the directional arrow of FIG. 17 which causes corresponding rotation of flange 28. Rotation of flange 28 in such direction results in distal translation of camming sleeve 64 through the cooperation of the threaded portions 34, 76 of the flange 28 and camming sleeve 64, respectively. As camming sleeve 64 distally translates, the distal end surface of the camming sleeve 64 engages outer surface portion 98a, 114a of retractor blades 98, 114 to cause the retractor blades 98, 114 to articulate via the camming action of the respective surfaces to the position depicted in FIG. 18. It is to be noted that retractor blades 98, 114 are preferably articulable through a range of about 0° to about 90° relative to the longitudinal axis "a" of instrument 10. Other ranges and articulated positions, e.g., 30°, 60°, etc . . . of the retractor blades 98, 114 are also contemplated.

With retractor blades 98, 114 articulated to the 90° position shown in FIG. 18, attention is directed to deploying, i.e., spreading the retractor blades 98, 114, i.e., causing relative movement of the retractor blades 98, 114 to retract the desired tissue. With reference now to FIG. 19, dual functioning control knob 20 is rotated in the direction indicated by the directional arrow depicted in FIG. 19 to cause corresponding rotation of control rod 24 and tissue penetrating member 122. Distal movement of control rod 24 is prevented by the smaller or first opening 40 of control button 36 as described above. Rotation of tissue penetrating member 122 causes blade mounting collar 86 to also rotate due to the engagement of the mounting section 130 of penetrating member 122 with the correspondingly dimensioned bore 108 of the blade collar 86. (FIG. 4A) In turn, rotation of blade collar 86 causes retractor blade 114 to move through an arc of rotation and away from retractor blade 98 from the position depicted in FIG. 20 to the position depicted in FIG. 22. It should be appreciated that alternatively both retractor blades 98, 114 can be rotated to an open (spaced-apart) position.

With particular reference to FIGS. 22–23, upon reaching its fully rotated position shown in FIG. 22, blade collar 86 is automatically locked in such position by the engagement of projections 120 of resilient clip 118 with locking grooves 112 defined in the proximal face of blade collar 86. (See also FIGS. 8–10) The cooperative engagement of clip 118 with blade collar 86 permanently locks blade collar 86 relative to retractor base 82 in a fully rotated position (as provided through the mounting of clip 118 to retractor base 82) thereby locking retractor blade 114 in its corresponding fully deployed position relative to retractor blade 98.

FIGS. 24–25 illustrates the retracting motion of retractor blade 114 in conjunction with a retracting procedure performed during a laparoscopic discectomy procedure. In FIGS. 24–25, instrument 10 is removed for illustrative purposes. As shown, retractor blades 98, 114, in the close approximated position, are disposed adjacent the aorta and vena cava. With reference to FIG. 25, control knob 20 is actuated to cause deployment of retractor blade 114 to its open position of FIG. 22 engaging and retracting vessel portions of the aorta and the vena cava thereby providing enhanced access to the underlying vertebra "v".

Figure 28:
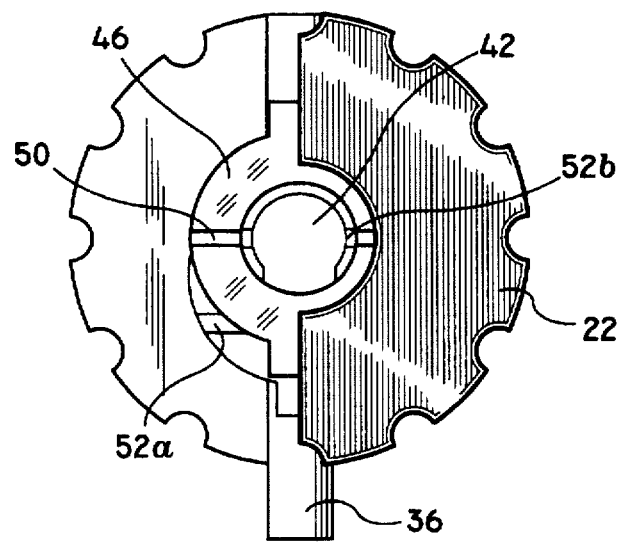
FIG. 28 is a cross-sectional view taken along the lines 28—28 of FIG. 26.

Referring now to FIGS. 26–29, with retractor blades 98, 114 fully deployed, attention is directed to deploying tissue penetrating member 122. Initially, control knob 20 is placed in its second operative mode by depressing control button 36 to cause the button to assume its second downward position of FIG. 26. In the second downward position, projecting tabs 50 of resilient clip 46 are received within the upper set of locking grooves of 52b of button 36 to securely retain the button 36 in this position. As best depicted in FIG. 28, with control button 36 in the second downward position, second opening 42 of the button 36 (FIG. 7) is in alignment with control rod 24, i.e., the control rod 24 passes through second opening 42 of switching button 36.

Figure 29:
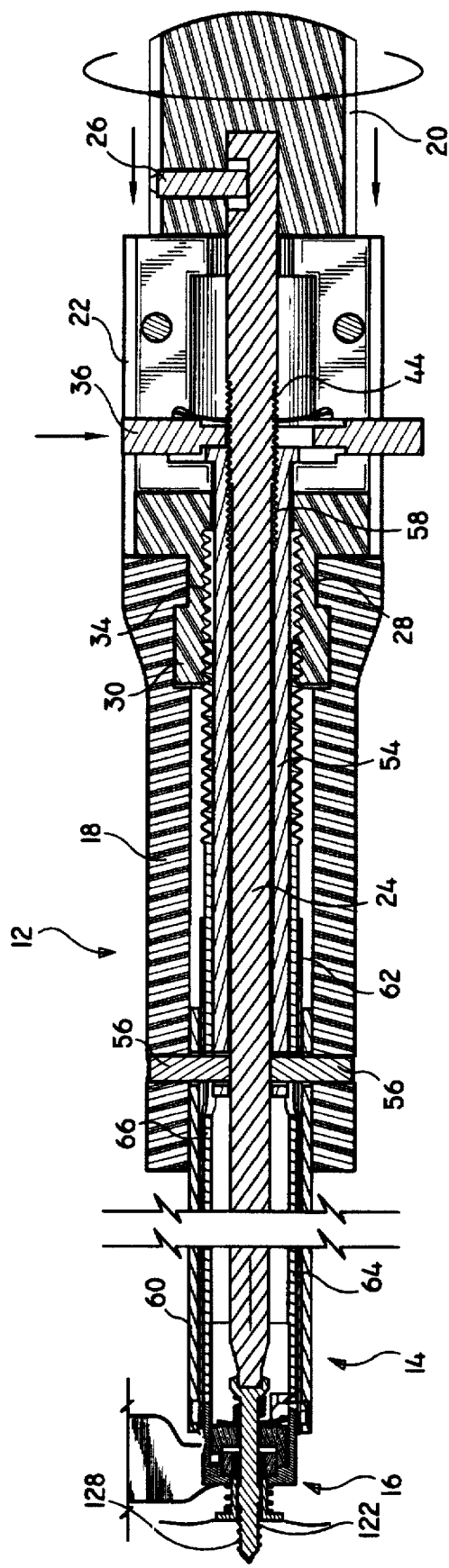
FIG. 29 is a side cross-sectional view of the instrument illustrating rotation of the control knob and corresponding axial movement of the control rod and the tissue penetrating member to deploy the tissue penetrating member into the vertebral bone.

Referring now to FIG. 29, control knob 20 is distally advanced by exertion of a distal force to the knob 20 to cause control rod 24 to also move distally for a limited distance. Distal movement of control rod 24 is made possible since the cross-sectional dimension of second opening 42 of control button 36 is greater than the cross-sectional dimension of threaded portion 44 of the control rod 24 thereby permitting the rod 24 to pass therethrough. Control rod 24 advances until threaded portion 44 engages internal threaded portion 58 of deployment sleeve 54. Thereafter, control knob 20 is rotated in the direction of the directional arrow depicted in FIG. 29, which causes control rod 24 to translate distally due to the cooperation of threaded portions 44, 58 of control rod 24 and deployment sleeve 54, respectively. Distal movement of control rod 24 results in the deployment of tissue penetrating member 122 into the tissue thereby mounting retractor 16 to the tissue. The outer threaded portion 128 of tissue penetrating member 122 facilitates penetration through hard tissue, e.g., the vertebrae.

Figure 30:
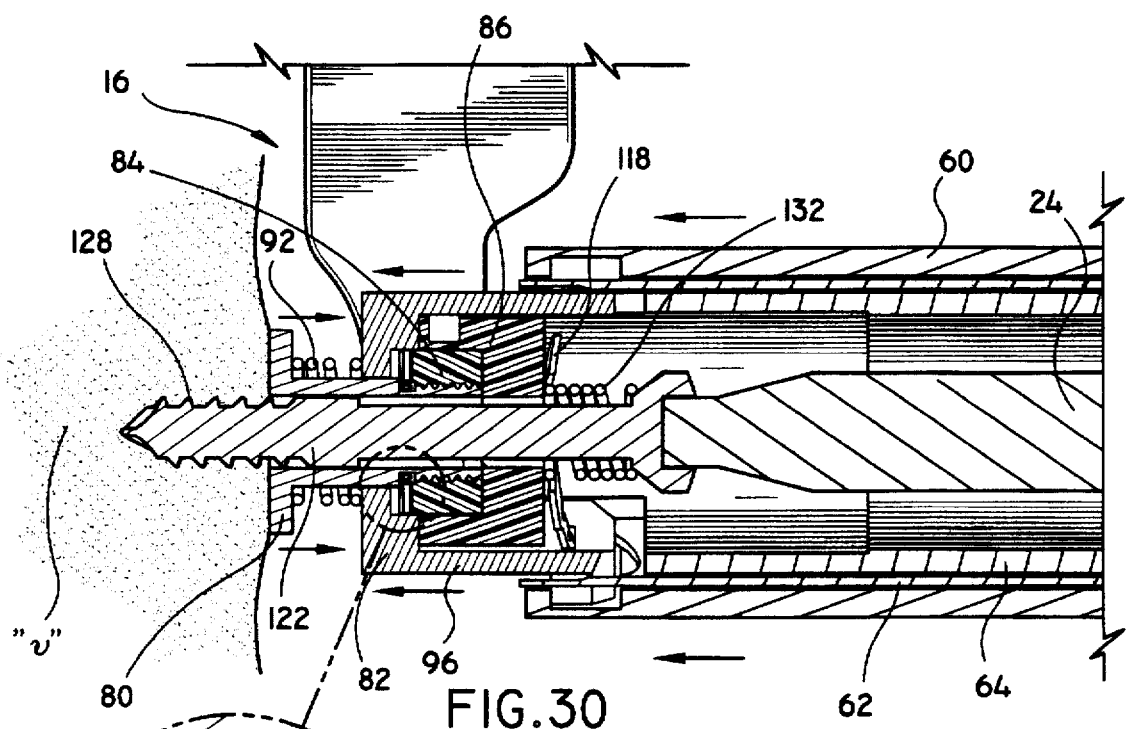
FIG. 30 is a side cross-sectional view of the distal end portion of the instrument illustrating the application of a distal force to permit adjusting movement of the open retractor blades through an angular section of rotation.
Figure 31:
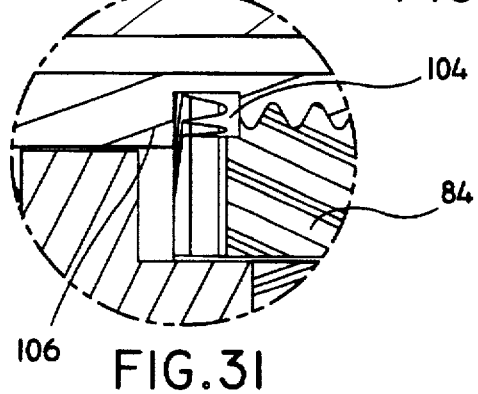
FIG. 31 is an isolated view illustrating the toothed collar released from the retractor base to permit the adjusting movement of the deployed retractor member.
Figure 32:
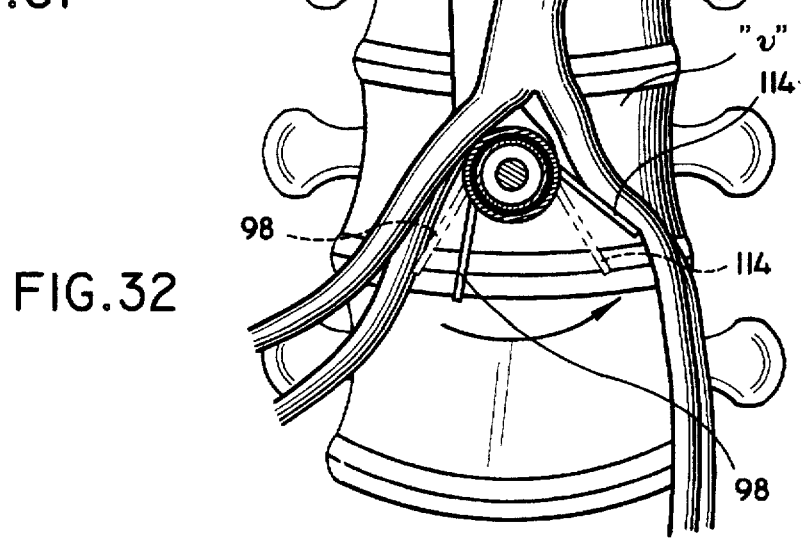
FIG. 32 is a view of a portion of the spinal column illustrating the retractor blades moved through an angular section of rotation.

Referring now to FIGS. 30–32, it may be desirable once tissue penetrating member 122 is fully deployed to adjust the positioning or angular orientation of the retractor blades 98, 114 of retractor 16. To achieve such readjustment movement of retractor 16, a distal force is exerted to handle portion 12. The resulting proximal counterforce provide by vertebral tissue "v" on retractor 16 causes proximal movement of locking cap 80 and toothed collar 84 against the bias of spring 92 as provided by slot 142 defined between the proximal face of toothed collar 84 and the distal face of mounting collar 86 as depicted in FIG. 4A. With toothed collar 84 moved proximally to the position depicted in FIG. 30, the external distal teeth 104 disposed on the distal face of toothed collar 84 become disengaged from locking projections 106 of retractor base 82 (FIG. 9) thereby permitting the retractor base 82 to rotate freely relative to locking cap 80 and toothed collar 84. The operator then rotates the instrument 10 which causes simultaneous rotation of retractor base 82 and blade mounting collar 86 (due to the locking engagement of clip 118 with the blade collar 86). Thus, retractor base 82 and mounting collar 86 rotate to adjust the angular orientation of blades 98, 114. FIG. 32 exemplifies such adjusting movement of retractor blades 98, 114.

Figure 33:
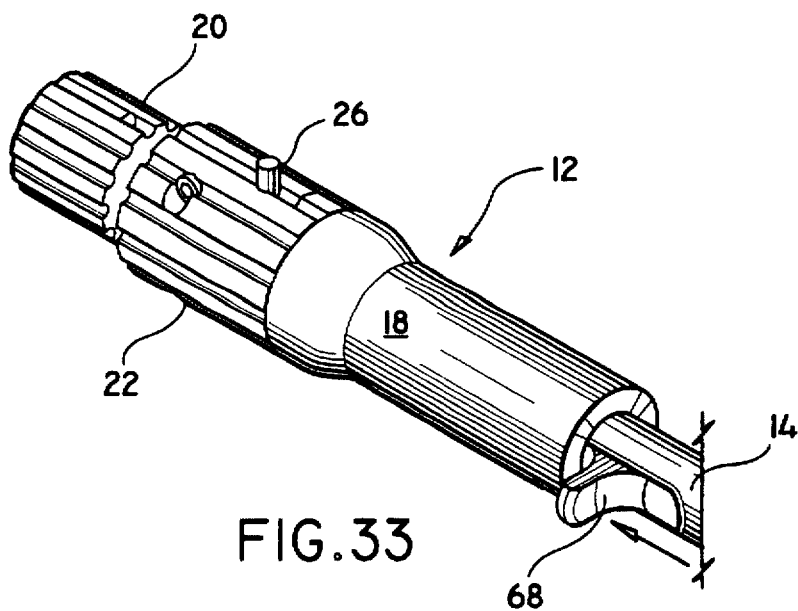
FIG. 33 is a perspective view illustrating movement of the release lever in the proximal direction.
Figure 34:
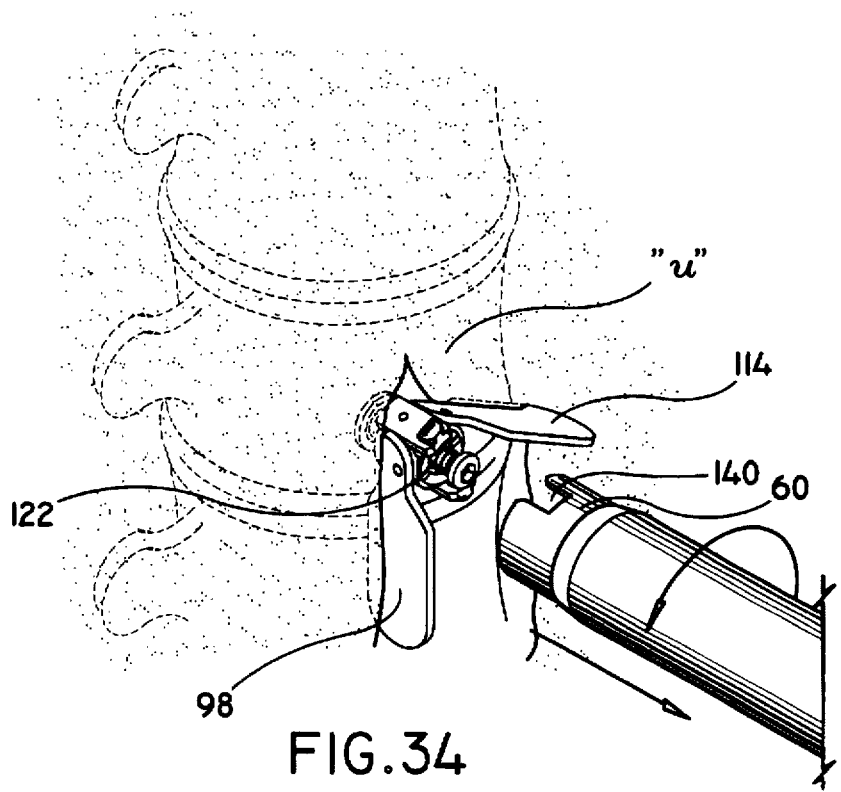
FIG. 34 illustrates release of the retractor member from the instrument.

With tissue penetrating member 122 deployed, retractor 16 can then be released from instrument 10. To release the retractor 16, release trigger 68 is moved proximally as depicted in FIG. 33 thereby causing proximal movement of locking sleeve 62 and release of mounting notches 140 from mounting heads 136 of retractor base 82. (FIG. 16) Thereafter, instrument 10 is rotated by rotating handle portion 12 such that mounting grooves 134 at the distal end of outer sleeve 60 become aligned with mounting wings 96 of retractor base 82, which alignment is depicted in FIG. 12. Once in alignment, the instrument 10 can be removed from retractor 10 and subsequently the operative site leaving retractor 16 mounted in the tissue as depicted in FIG. 34. It is to be noted that tissue penetrating member 122 is released from its engagement with distal head 124 of control rod 24 during release of retractor 16. FIG. 34 illustrates the instrument 10 inserted within a trocar "t" with the retractor 16 released and engaging spinal muscle.

Thus, retractor 16 remains mounted to the vertebrae during the surgical procedure to retract the tissue and improve access to the surgical site. At the end of the procedure, e.g., removal of the disc and, possibly, insertion of a fusion implant, the instrument may be reinserted through the trocar "t" and into the body cavity to retrieve retractor 16 and remove the retractor from the operative site. In particular, distal hexagonal-head 126 of control rod 24 is positioned within hexagonal recess 126 of tissue penetrating member 122. Control knob 20 is rotated in a direction opposite to the direction shown in FIG. 29 to unscrew the tissue penetrating member 122 from the vertebrae. Thereafter, control knob 20 is pulled proximally to the position depicted in FIG. 19 and control button 36 is returned to its first position. Control knob 20 is rotated in the direction opposite to the direction shown in FIG. 19 to cause blades 98, 114 to return to the closed approximated position of FIG. 20. Articulating knob 22 in then rotated in an opposite direction to that shown in FIG. 17 to articulate blades 98, 114 to their normal aligned position of FIG. 14 for withdrawal of the instrument from the trocar.

Alternate Embodiment

Figure 35:
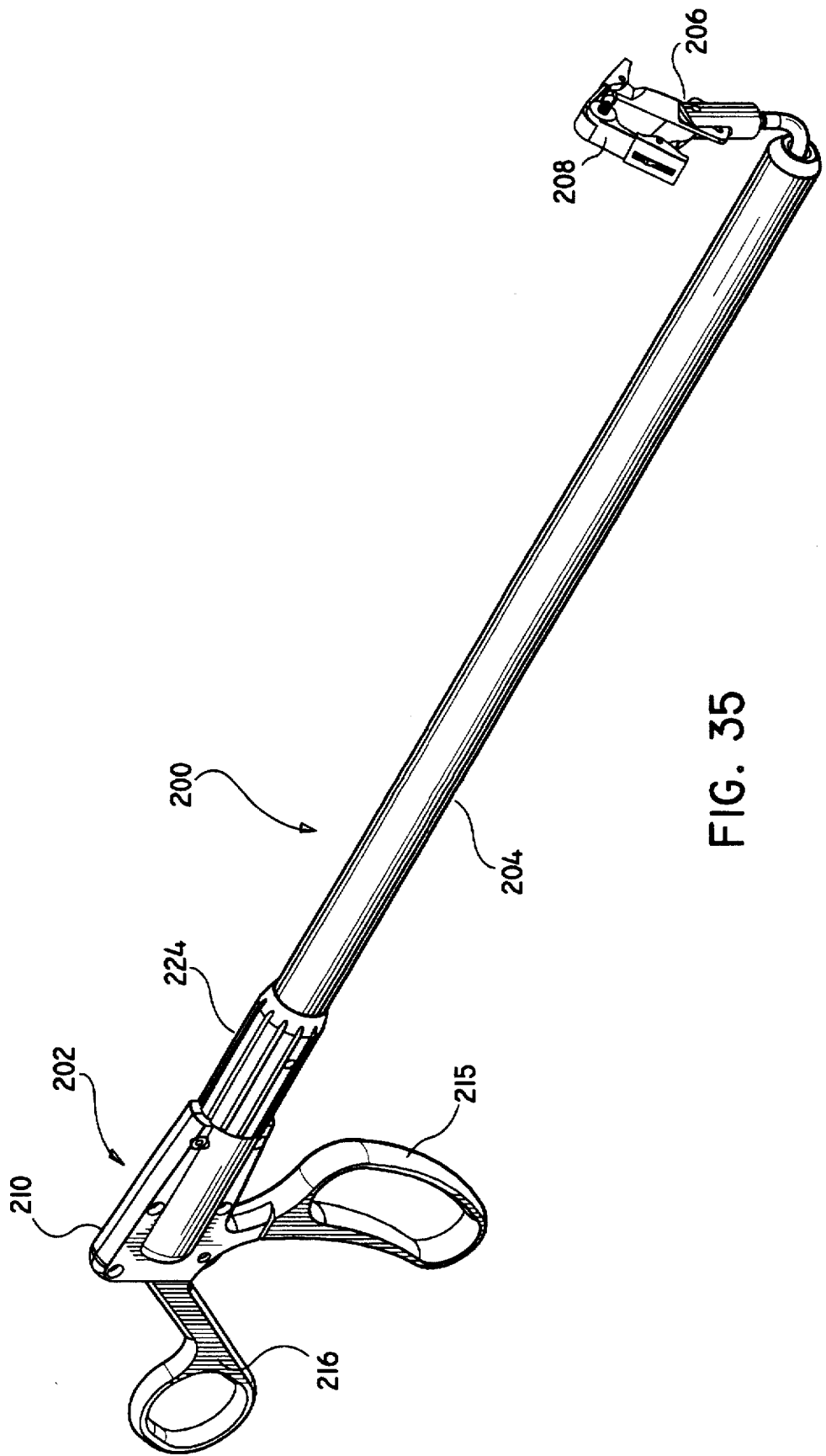
FIG. 35 is a perspective view of an alternate embodiment of the present disclosure.

Referring now to FIG. 35, there is illustrated an alternate embodiment of the instrument of the present disclosure. Instrument 200 is also specifically contemplated for use during spinal surgery in retracting tissue, but, may have alternative applications as well. Instrument 200 includes handle 202 and elongated portion 204 connected to the handle 202 and extending distally therefrom. Instrument 200 further includes retractor deployment mechanism 206 at the distal end of elongated portion 204 and an associated retractor 208 which is releasably mounted to the deployment mechanism 206.

Figure 36:
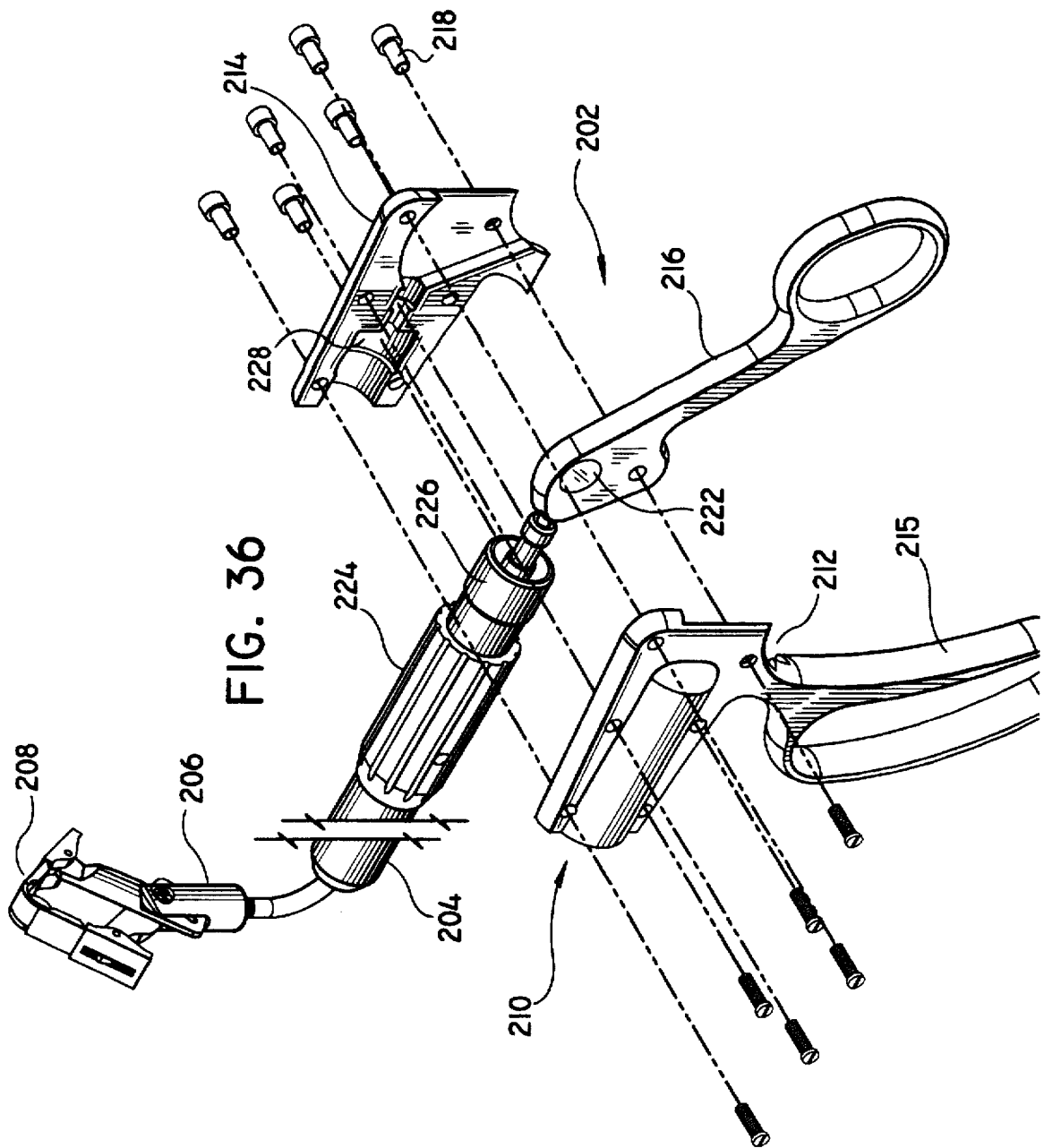
FIG. 36 is a perspective view with parts separated of the handle portion of the instrument of FIG. 35.
Figure 37:
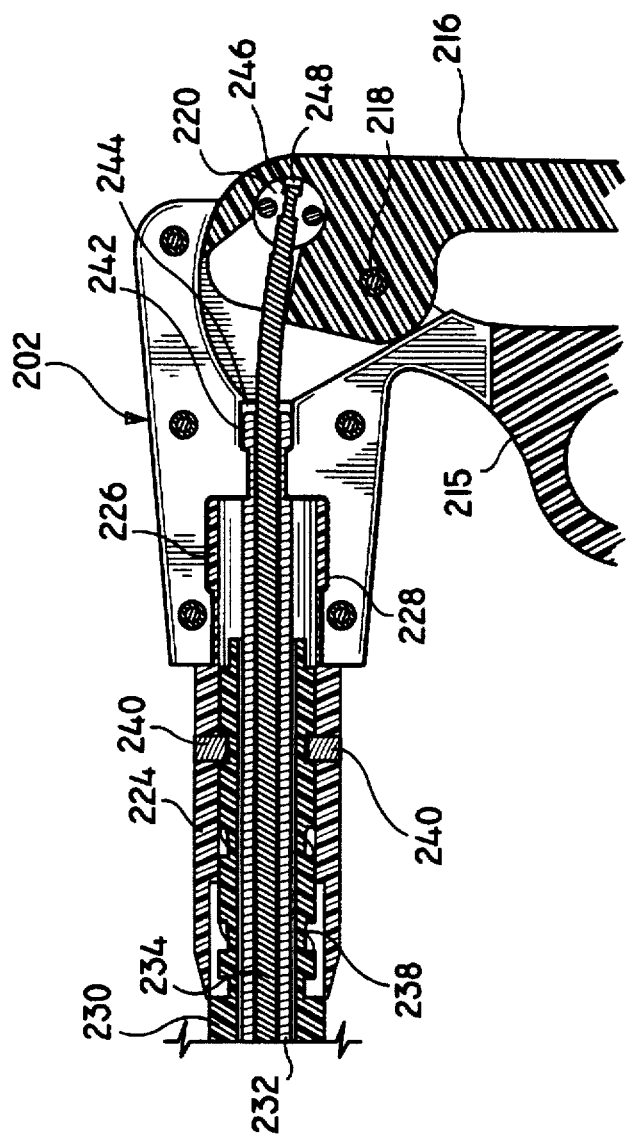
FIG. 37 is a side cross-sectional view of the handle portion of the instrument.

Referring now to FIGS. 35–37, handle 202 includes housing 210 having housing half sections 212, 214 secured to each other by screws or the like. Half section 212 has stationary finger grip 215 integrally formed therewith. A movable grip 216 is pivotally mounted to housing 210 about pivot pin 218. Handle 202 further includes a rod mounting disk 220 (FIG. 37) which is accommodated within a corresponding aperture 222 defined in movable grip 216. Mounting disk 220 may be fixedly secured within aperture 222 with the use of adhesives or the like. A manually rotatable knob 224 is mounted to the forward portion of housing 210. In a preferred embodiment, rotatable knob 224 incorporates a mounting flange or collar 226 which is received within a correspondingly dimensioned recess 228 defined in the housing to rotatably mount the knob 224. Rotatable knob 224 preferably has a scalloped exterior to enhance grasping engagement by the user.

Figure 38:
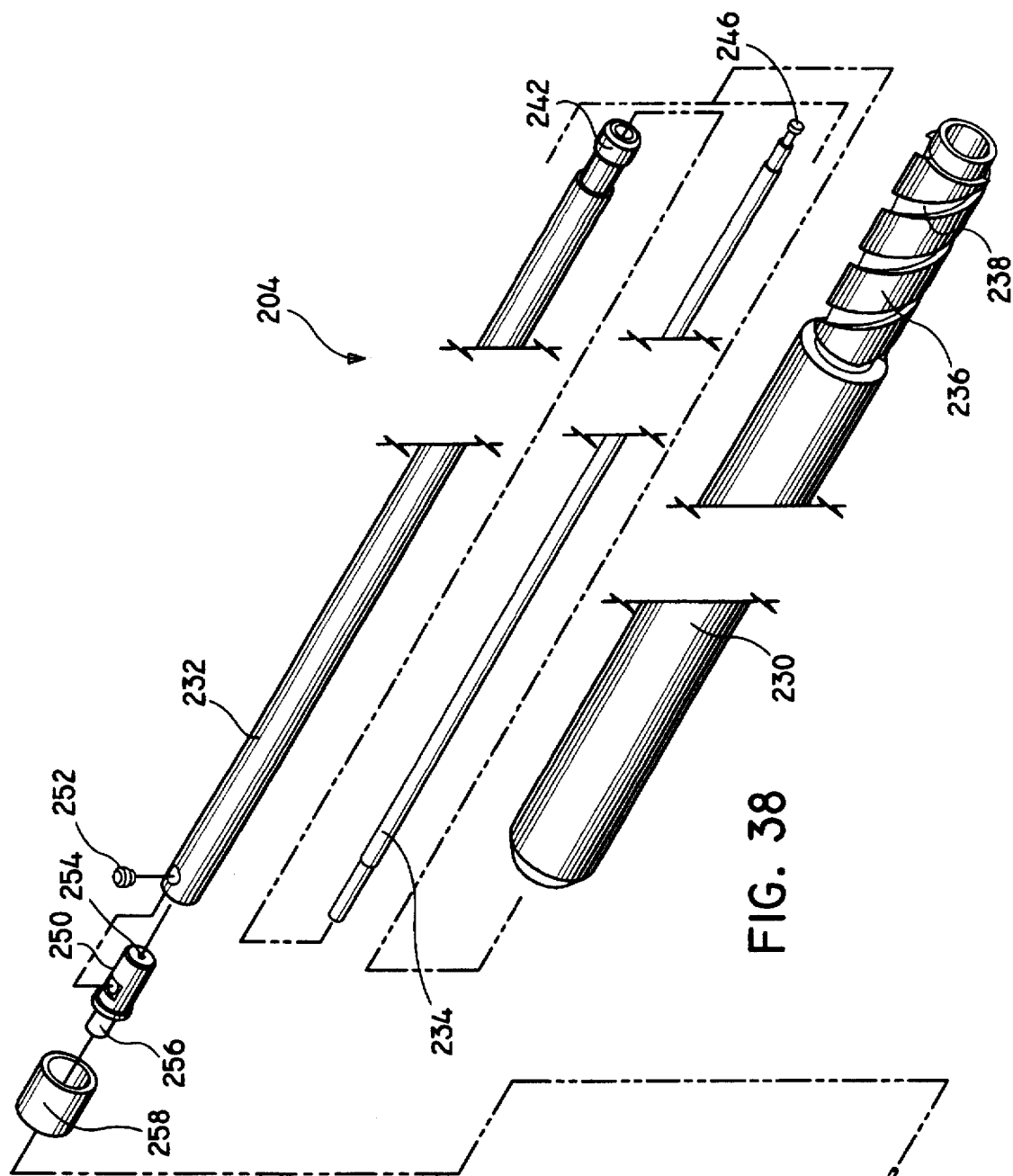
FIG. 38 is a perspective view with parts separated of the elongated portion of the instrument.

Referring now to FIGS. 37–38, elongated portion 204 includes outer sleeve 230, inner sleeve 232 and central control rod 234. Outer sleeve 230 possesses proximal portion 236 having a camming groove 238 defined in its outer surface. Outer sleeve 238 is operatively connected to rotatable knob 224 through opposed camming pins 240 which are mounted to the knob 224 and extend within camming groove 238. (FIG. 37) In this manner, rotation of rotatable knob 224 causes outer sleeve 230 to translate accordingly as effectuated through the camming action of camming pins 240 with camming groove 238. Inner sleeve 232 is mounted to housing 210 through the interfitting relation of proximal collar 242 with correspondingly dimensioned recess 244 defined in the assembled housing half sections 212, 214.

Control rod 234 is operatively connected to movable grip 216 through the cooperative engagement of proximal mounting head 246 with a correspondingly dimensioned mounting recess 248 defined in mounting disk 220. Control rod 234 is reciprocally longitudinally movable within inner sleeve 232 in response to corresponding pivoting movement of movable grip 216.

Figure 39:
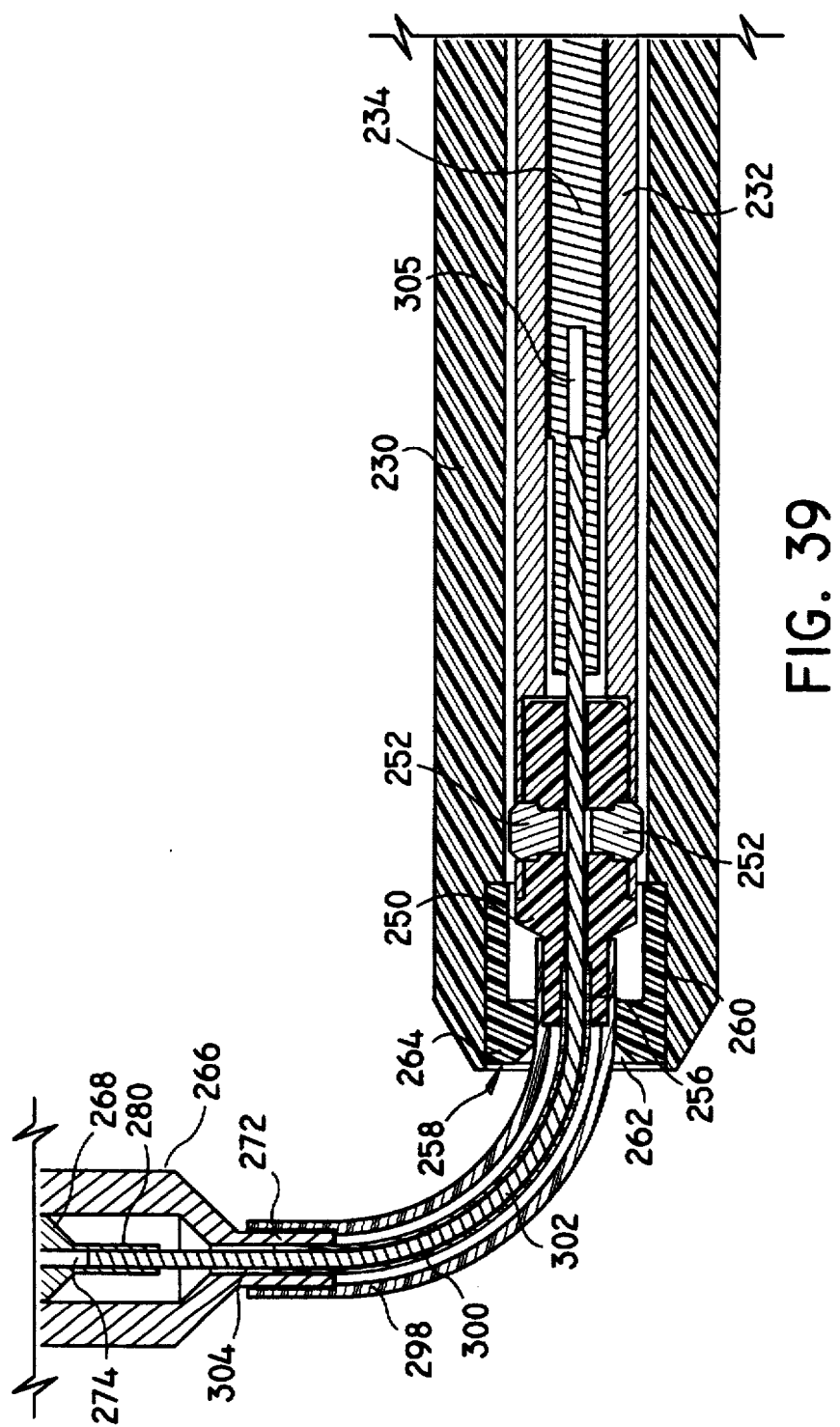
FIG. 39 is a side cross-sectional view of the distal end portion of the elongated portion.

Referring now to FIGS. 38–39, elongated portion 204 further includes mounting tip member 250 which is positioned within the distal end portion of inner sleeve 232 of elongated portion 204 and is secured within the inner sleeve 232 by set screws 252. Tip member 250 defines an internal bore 254 and distal mounting collar 256. A cylindrical bushing 258 is positioned within a correspondingly dimensioned recess 260 defined in outer sleeve 230 and is secured within the sleeve 230 with the use of adhesives. Bushing 258 has an inner bore portion 262 at its distal end as defined between radially inwardly extending wings 264. (FIG. 39)

Referring now to FIGS. 35 and 40–43, the retractor deployment mechanism 206 and associated retractor 208 will be discussed. Retractor deployment mechanism 206 includes main yoke 266, minor yoke 268 slidably positioned within the main yoke 266 and interleaved retractor mounting members 270. Main yoke 266 has proximal collar portion 272 with a generally reduced diameter and inner recess 274 defining opposed fingers 276. (FIG. 42) Each finger 276 possesses an aperture 278 formed therein in alignment with the aperture 278 of the other finger 276. Minor yoke 268 includes proximal collar portion 280 and yoke fingers 282 defining recess 284 therebetween. (FIG. 43) Fingers 280 also include aligned apertures 286.

Retractor mounting members 270 include cam slots 288 defined in their proximal end portions. A cam pin 290 traverses apertures 286 of minor yoke 268 and cam slots 288 to operatively connect the minor yoke 286 and the retractor mounting members 270. Retractor mounting members 270 further include generally centrally disposed mounting apertures 292. A screw 294 extends through apertures 278 of yoke fingers 276 and apertures 292 of mounting members 270 to connect main yoke 266 and the mounting members 270. (FIG. 42) Retractor mounting members 270 further include mounting grooves 296 formed at their distal ends, the significance of which will be discussed hereinbelow.

Referring now to FIGS. 39–43, deployment mechanism 206 further includes outer tube 298, inner guide tube 300 disposed within the outer tube 292 and drive rod 302 mounted within the inner tube 300. Outer tube 298 is mounted at its distal end to main yoke 266. In a preferred mounting arrangement, a distal end portion of outer tube 298 is positioned onto proximal collar portion 272 of main yoke 266 with the distal tube portion preferably being adhered to the collar portion 272 to effectuate the mounting. (FIG. 39) Other mounting arrangements are envisioned as well. Similarly, outer tube 298 is mounted at its proximal end to distal mounting collar 256 of mounting tip member 250 by the use of adhesives or the like.

Outer tube 298 is preferably fabricated from a shape memory material such as Tinel and is movable between a normal unstressed curved configuration depicted in FIGS. 39–40 to a stressed generally linear configuration.

Inner guide tube 300 is fabricated from a flexible material such as Tinel and serves in guiding drive rod 302 during longitudinal movement thereof. The distal end portion of inner guide tube 300 is positioned within bore 304 defined in collar portion 272 of main yoke 266 and may be secured within the bore by the use of adhesives, a crimping operation, etc . . . (FIG. 39) The proximal end portion of inner guide tube 300 is secured within internal bore 254 of mounting tip member 250.

Drive rod 302 is connected at its distal end to minor yoke 268 by the reception of the distal end of the drive rod 302 within a bore defined in proximal collar portion 280 of the minor yoke 268 and at its proximal end to control rod 234 by the reception of the drive rod within bore 305 of the control rod (FIG. 39). Drive rod 302 is fixedly secured to both these components with the use of adhesives or the like. Drive rod 302 is adapted for reciprocal longitudinal movement and, as stated above, is guided during such movement by guide tube 300. Drive rod 302 is fabricated from a flexible material so as to assume the curved orientation of guide tube 300 and outer tube 298, but, has sufficient rigidity to translate a distal force to the minor yoke 268.

Figure 44:
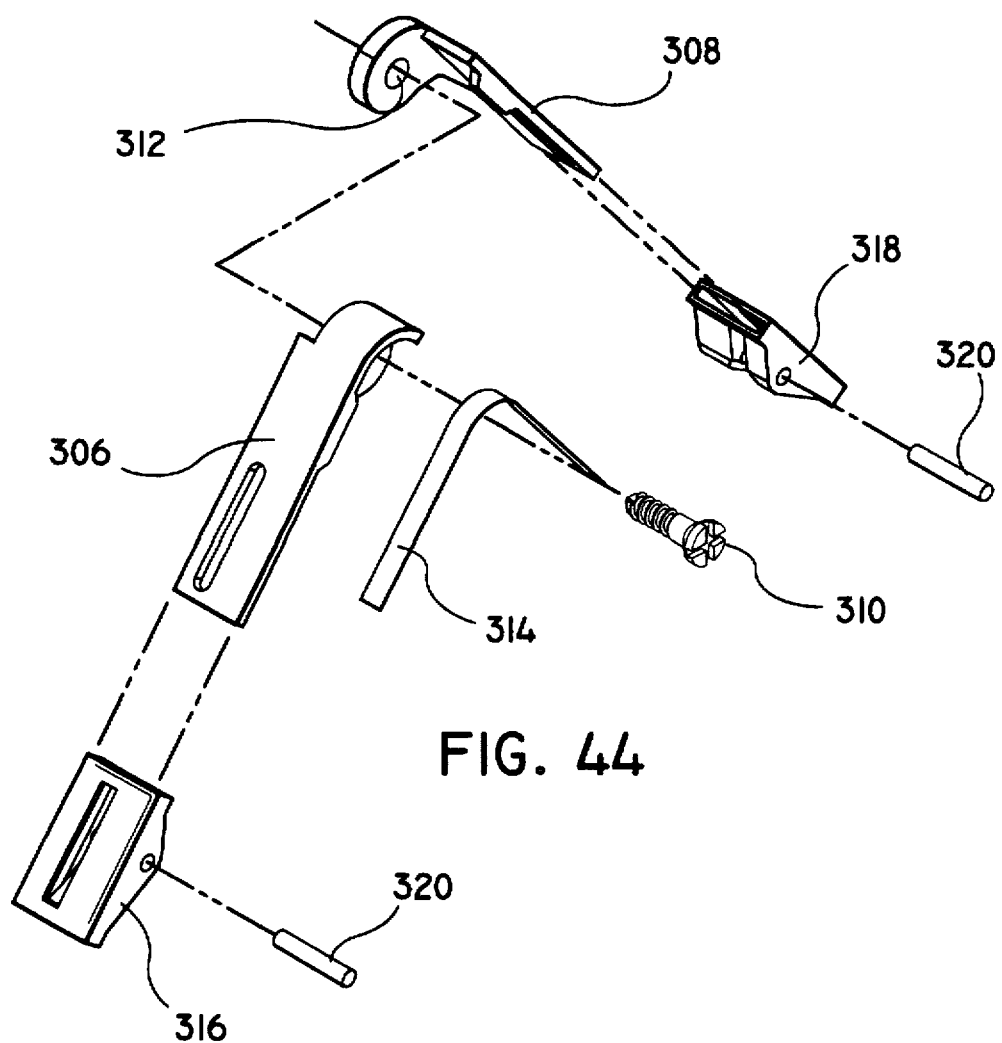
FIG. 44 is a perspective view with parts separated of the retractor.
Figure 45:
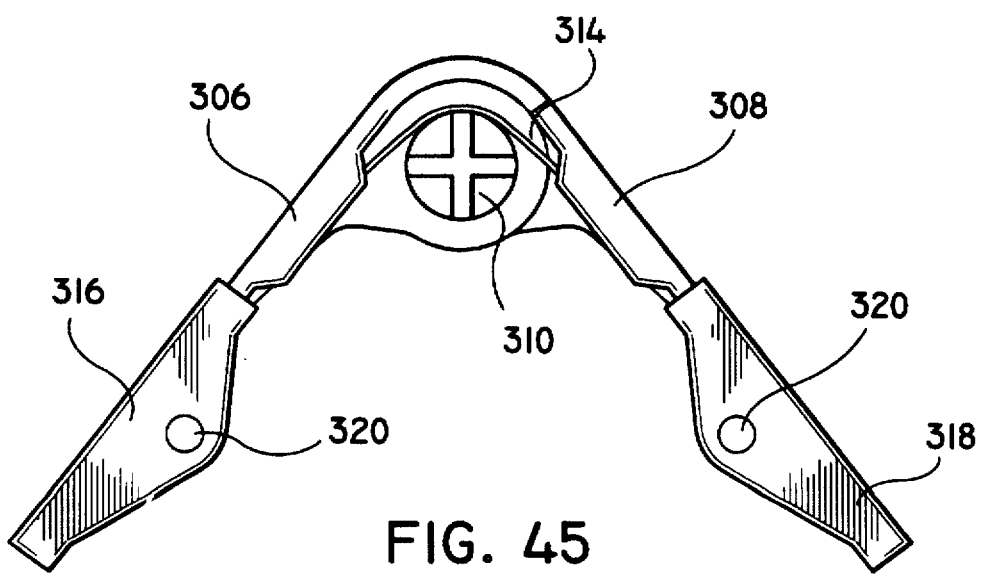
FIG. 45 is a plan view of the retractor.

Referring now to FIGS. 41 and 44–45, retractor 208 includes first and second retractor arms 306, 308 pivotally connected to each other about connecting screw 310 which traverses apertures 312 of the arms 306, 308. Connecting screw 310 has an external threaded portion capable of penetrating hard tissue. A resilient leaf spring 314 extends across retractor arms 306, 308 and is positioned within a space defined between connecting screw 310 and retractor arm 306. Leaf spring 314 is normally biased to a generally linear configuration. Brackets 316, 318 are respectively mounted to retractor arms 306, 308. Each bracket 316, 318 has a mounting pin 320 secured thereto.

Figure 46:
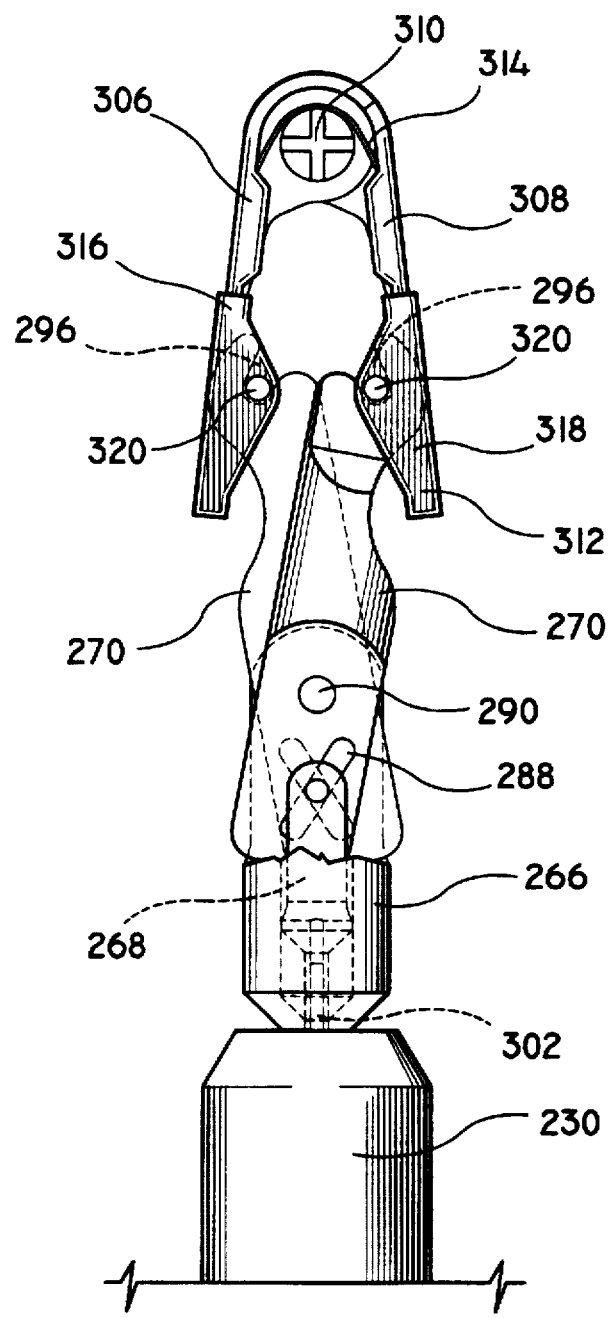
FIG. 46 is a plan view illustrating the retractor in the closed position.

With reference to FIGS. 41 and 44–46, retractor 208 is releasably mounted to mounting members 270 through the reception of mounting pins 320 within mounting grooves 296 of the members 270. Retractor 208 is movable between the open position depicted in FIG. 45 and the closed position depicted in FIG. 46. Leaf spring 314 normally biases retractor arms 306, 308 to the open position. In the closed position of FIG. 46, the radial outward force provided by leaf spring 314 forces retractor arms 306, 308 outwardly thereby driving mounting pins 320 within mounting grooves 296 of mounting members 270. As best depicted in FIG. 46, the radially outward bias of mounting pins 320 in conjunction with the inclined orientation of mounting grooves 296 (with retractor 208 in the closed position) of mounting members 270 effectively results in mounting engagement of the retractor 208 and mounting members 270.

Operation

Figure 47:
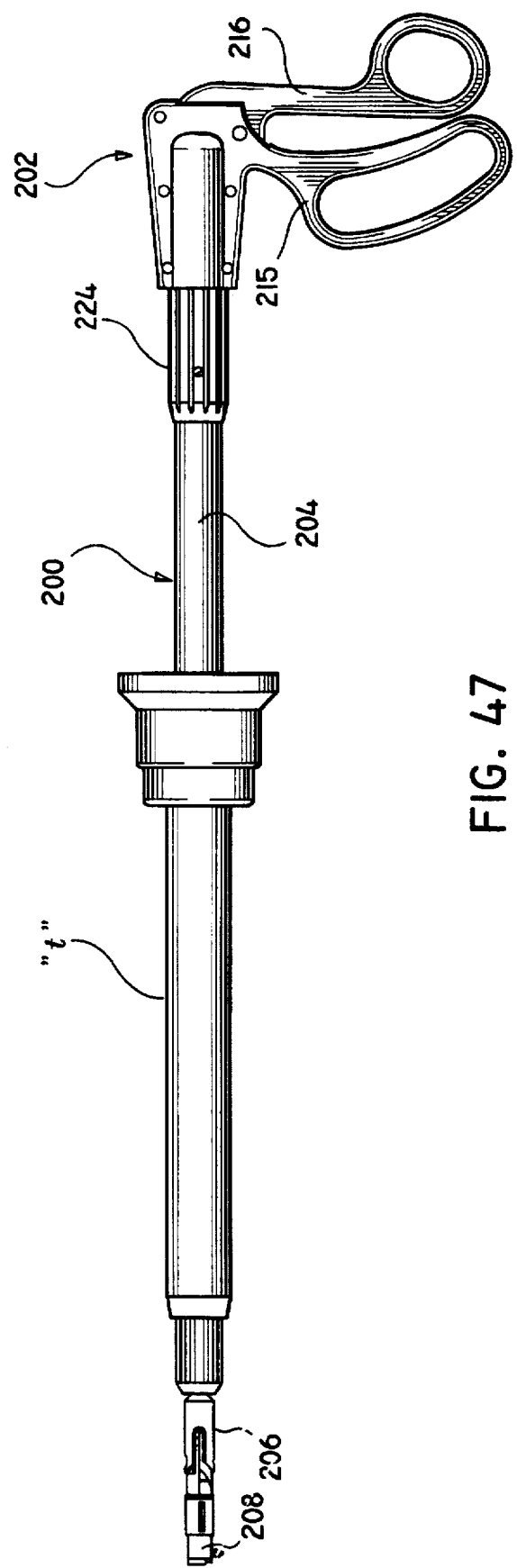
FIG. 47 is a plan view of the instrument positioned within a conventional trocar with the retractor in the closed position.

The operation of instrument 200 will now be discussed. The instrument in the non-actuated condition of FIG. 47 is positioned within a conventional trocar "t" accessing the abdominal cavity and advanced to a location adjacent the targeted site. With reference to FIGS. 48–49, rotatable knob 224 is rotated in the direction of the directional arrows of FIGS. 48–49 thereby causing retracting movement of outer sleeve 230 through the camming action of camming pins 240 within camming groove 238 (FIGS. 37–38). Once outer sleeve 230 retracts to a position where outer tube 298 is no longer disposed within the outer sleeve 230 (i.e., with the constraining effect of outer sleeve 230 removed), outer tube 298 is permitted to assume its normal unstressed curved configuration as effectuated through the inherent shape memory characteristics of its material of fabrication.

Figure 50:
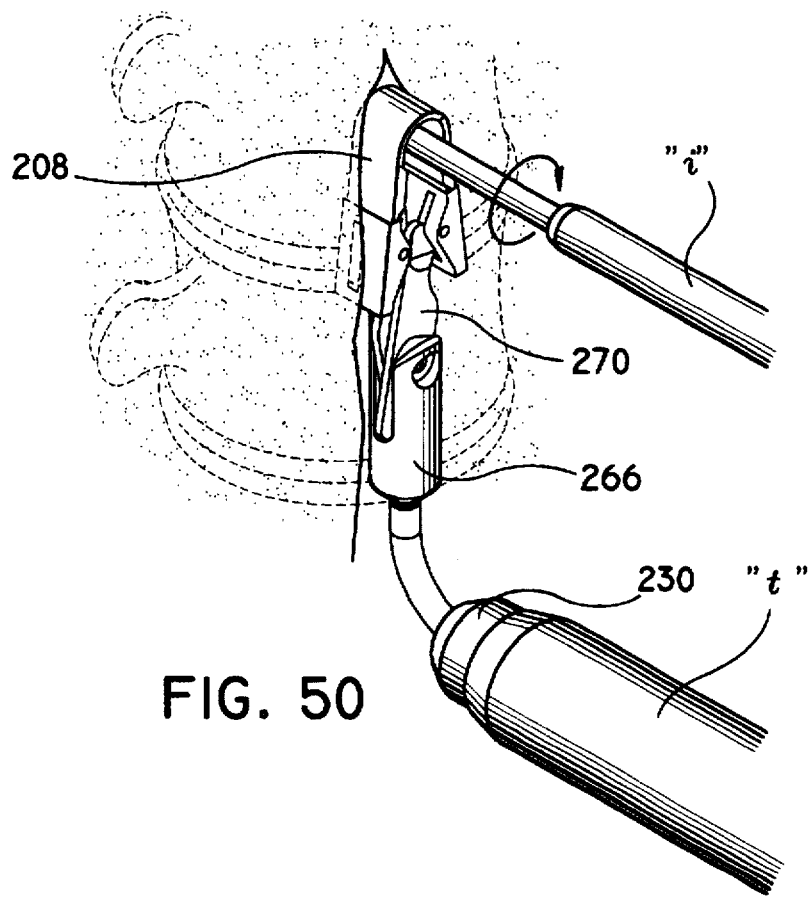
FIG. 50 is a perspective view illustrating positioning of the retractor within tissue and deployment of the tissue penetrating member.
Figure 51:
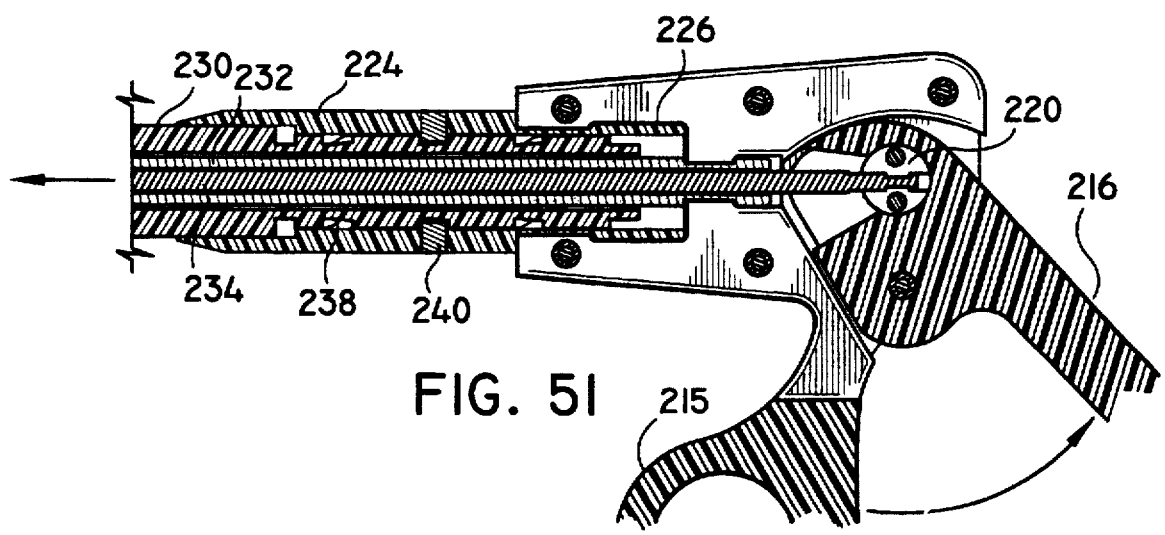
FIG. 51 is a side cross-sectional view similar to the view of FIG. 49 illustrating actuation of the trigger to cause movement of the retractor blades.
Figure 52:
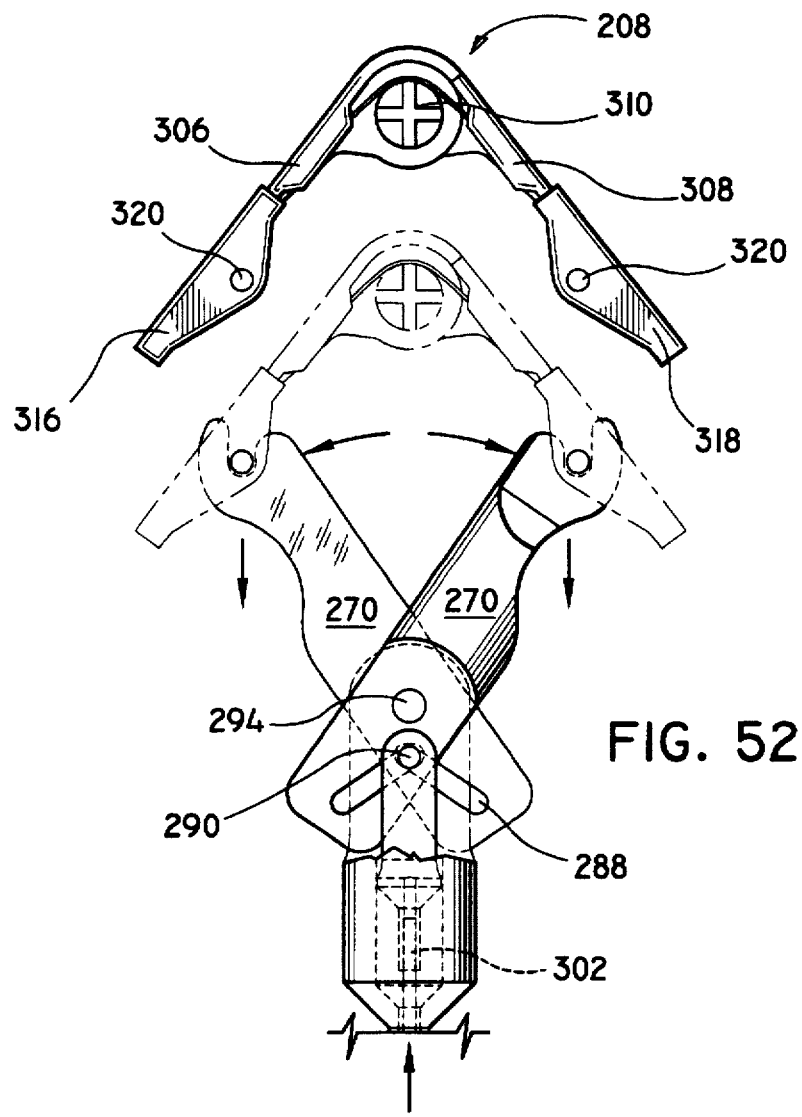
FIG. 52 is a plan view illustrating release of the retractor from the deployment mechanism.
Figure 53:
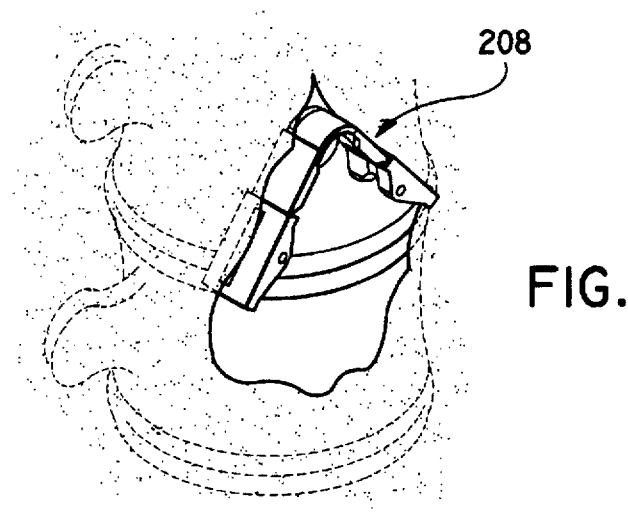
FIG. 53 is a perspective view of the retractor deployed in the tissue.

With reference now to FIG. 50, which depicts retractor positioned adjacent the vertebral column and engaging spinal muscle, an applicator tool "i" is utilized to drive bone screw 310 (FIGS. 43 and 44) into the vertebrae. Any applicator tool "i" suitable for this purpose may be utilized provided the tool "i" has an instrument head corresponding to the head of screw 310. As depicted in FIG. 51, moveable grip 216 is pivoted in the direction shown in FIG. 51 resulting in corresponding distal movement of central control rod 234 and advancing movement of drive rod 302. With reference to FIG. 52, such movement of drive rod 302 advances minor yoke 268 within main yoke 266 to thereby cause cam pin 290 to traverse cam slots 288 and, as a result of the camming action, effectuate the opening of retractor 208 as depicted in FIG. 52. It is also to be noted that in the open position of retractor members 270, mounting pins 320 may release from mounting grooves 296 of the mounting members 270 thereby releasing retractor 208 as shown in FIG. 52. In such open position depicted in FIG. 53, retractor 208 engages and spreads the spinal tissue thereby providing enhanced access to the underlying vertebral site for subsequent operative procedures.

With retractor 208 fully deployed and mounted to the vertebral column in the aforedescribed manner, instrument 200 may be removed from the operative site. With reference to FIG. 54, rotatable knob 224 is rotated in the direction indicated by the directional arrow thereby causing outer sleeve 230 to advance via the camming action of camming pin 240 within camming groove 238. During such movement, outer sleeve 230 passes over shape memory outer tube 298 resulting in the tube 298 being stressed to a generally straight configuration contained within outer sleeve 230. Thereafter, instrument 200 is removed from the trocar as depicted in FIG. 55 to permit the introduction of additional surgical instruments to conduct the desired surgery with arms 306, 306 retracting the surrounding tissue to improve visibility and access to the surgical site.

At the end of the procedure, instrument 200 is reinserted through the trocar and into the body to retrieve retractor 208. Once inserted, knob 224 is rotated to retract outer sleeve 230 to enable tube 298 to assume its curved configuration as discussed above. Moveable grip 216 is then pivoted to spread mounting members 270 and the instrument is positioned so that mounting grooves 296 of mounting members 270 engage mounting pins 320 of retractor 208. Connecting screw 310 is removed with applicator tool "i". Movable grip 216 is released to return to its open position to close mounting members 270 and retractor arms 306, 308, and knob 224 is rotated to advance outer sleeve 230 to straighten tube 298. Instrument 200 is then withdrawn through trocar "t".

As stated above, the surgical instruments of FIGS. 1–55 have particular application in conjunction with an anterior endoscopic lumbar discectomy. When performing an anterior endoscopic lumbar discectomy, the patient is placed in the supine position and entry is made through the abdomen, which is insufflated according to known procedures. Specific points of entry are determined by the particular intervertebral disc to be removed. For removal of intervertebral discs of the lumbar vertebrae, ports or trocars are established in the lower abdomen using standard trocars. One port is dedicated to viewing via an endoscope, while remaining ports are used for surgical instrument insertion and manipulation.

To access the intervertebral disc, soft tissue is dissected providing a pathway through the abdominal region. Fascia and other soft tissue may be spread using a surgical retractor or tissue spreader. Organs such as the colon are retracted away from the operating site to increase exposure and facilitate observation of the spinal column.

Upon reaching the spinal column, blunt dissection is performed to expose the intervertebral disc. Fascia is removed from the disc area and spread using the retractor of FIG. 1 and/or FIG. 35 disclosed herein which is directly mounted to the vertebral body. As appreciated, the retractor permits enhanced access to the vertebral area while occupying minimal space. In addition, once deployed and mounted to the vertebral column, the retractors do not require continued manipulation by the surgeon.

The herniated disc nucleus is accessed through the disc annulus. The disc annulus may be incised using a conventional endoscopic cutting instrument. Such instrument includes for example endoscopic scissors or rongeurs. A portion of the disc annulus may be removed to form an access channel, or, an incision may be created and the incision edges spread open through the tissue spreading element. Alternatively, the disc annulus may be incised using a laser or an access port created using a trephine.

A cutting instrument is inserted into the disc nucleus. Following insertion into the disc nucleus, the cutting instrument slices away portions of the disc nucleus, which may be removed using forceps, rongeurs, or suction instruments. Other instruments may be selected for disc removal including lasers, rongeurs, and the like. Using the anterior approach, as much or as little of the herniated nucleus may be removed as needed to alleviate compression of the adjacent muscles and nerves. This surgical procedure permits the surgeon to directly monitor the disc removal process by means of an endoscope.

It is further to be appreciated that the retractors of the present disclosure can be used for facilitating other endoscopic (minimally invasive) surgical procedures such as spinal fusion. Spinal fusion is used to stabilize spinal segments and is currently performed using fusion baskets, bone plugs or other internal fixation device. A known spinal fusion implant and associated method is disclosed in U.S. Pat. No. 4,961,740 to Ray.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical apparatus, which comprises:
   a) an elongated portion defining a generally longitudinal axis and having proximal and distal end portions;
   b) first and second retractor members disposed at the distal end of the elongated portion for engaging and spreading tissue, the retractor members adapted for relative movement between a first generally approximated position and a second generally open position, the retractor members being spring biased to the open position;
   c) an articulating mechanism operatively connected to the retractor members, the articulating mechanism actuable to selectively articulate the retractor members; and
   d) an actuator mechanism operatively connected to the retractor members, the actuator mechanism actuable to cause relative movement between the retractor members.

2. The surgical apparatus according to claim 1 further including a release member operatively connected to the retractor members and movable to release the retractor members from the distal end portion of the elongated portion.

3. A surgical apparatus, which comprises:
   a) an elongated portion defining a generally longitudinal axis and having proximal and distal end portions;
   b) first and second retractor members disposed at the distal end portion of the elongated portion for engaging and spreading tissue, the retractor members being releasably mounted to the distal end portion of the elongated portion;
   c) an articulating mechanism operatively connected to the retractor members, the articulating mechanism actuable to selectively articulate the retractor members; and
   d) an actuator mechanism operatively connected to the retractor members, the actuator mechanism actuable to cause relative movement between the retractor members; and
   e) a release mechanism operatively associated with the retractor members, the release mechanism actuable to release the retractor members from the distal end portion of the elongated portion.

4. The surgical apparatus according to claim 3 including a tissue penetrating member associated with the retractor members, the tissue penetrating member mounted for movement to facilitate mounting of the retractor members to tissue.

5. The surgical apparatus according to claim 4 wherein the retractor members are connected to the distal end portion of the elongated portion by a connector member, the connector member including a memory material, the connector member being movable between a stressed condition and an unstressed condition, wherein in the unstressed condition the connector member positions the retractor members in articulated relation with respect to the longitudinal axis.

6. The surgical apparatus according to claim 5 including a manually movable member operatively engageable with the connecting member, the manually movable member movable to move the connecting member between the unstressed and stressed condition.

7. The surgical apparatus according to claim 6 wherein the manually movable member is a proximally positioned rotatable member.

8. The surgical apparatus according to claim 5 wherein the retractor members are connected to each other, the retractor members being movable between a closed position and an open position.

9. The surgical apparatus according to claim 8 wherein the retractor members are normally spring biased to the open position.

10. The surgical apparatus according to claim 9 including a manually movable member for moving the retractor members between the open position and closed position.

11. The surgical apparatus according to claim 10 wherein the manually movable member is a proximally positioned lever grip.

12. The surgical apparatus according to claim 4 wherein the tissue penetrating member is releasably mounted to the distal end portion of the elongated portion, the tissue penetrating member movable between a non-deployed position and a deployed position wherein in the deployed position the tissue penetrating member engages tissue thereby facilitating mounting of the retractor members in the tissue.

13. The surgical apparatus according to claim 12 including a deployment mechanism operatively associated with the tissue penetrating member, the deployment mechanism actuable to move the tissue penetrating member to the deployed position.

14. The surgical apparatus according to claim 13 wherein the release mechanism is operatively associated with the tissue penetrating member such that actuation of the release mechanism causes release of the retractor members and the tissue penetrating member.

15. The surgical apparatus according to claim 13 wherein the deployment mechanism is operable by a proximally positioned rotatable member.

16. The surgical apparatus according to claim 14 wherein the release mechanism is operable by a proximally positioned release lever.

17. The surgical apparatus according to claim 12 including a rotation mechanism, the rotation mechanism actuable to rotate the retractor members through a predetermined angular sector of rotation.

18. The surgical apparatus according to claim 12 wherein the first retractor member is adapted to move upon actuation of the actuation mechanism and wherein the second retractor member is stationary upon actuation of the actuation mechanism.

19. The surgical apparatus according to claim 12 wherein the actuator mechanism is operable by a proximally positioned manually rotatable member.

20. The surgical apparatus according to claim 12 wherein the articulating mechanism is operable by a proximally positioned manually rotatable member.

21. A surgical apparatus, which comprises:
   a) a handle portion dimensioned to be grasped by the hands of a user;
   b) an elongated portion connected to the handle portion and extending distally therefrom, the elongated portion defining a longitudinal axis and having proximal and distal end portions;

c) at least two retractor blades releasably mounted to the distal end portion of the elongated portion, the retractor blades being adapted for relative movement;

d) a tissue penetrating member operatively associated with the retractor blades and releasably mounted to the distal end portion of the elongated portion, the tissue penetrating member movable to a deployed position to engage tissue; and e) an actuator member operatively connected to the retractor blades, the actuator member movable relative to the elongated portion to cause relative movement of the retractor blades.

22. The surgical apparatus according to claim 21, wherein the tissue penetrating member is releasably mounted to the distal end portion of the elongated portion.

23. The surgical apparatus according to claim 22, further comprising a release mechanism operatively associated with the retractor blades and the tissue penetrating member, the release mechanism actuable to release the retractor blades and the tissue penetrating member from the distal end portion wherein the tissue penetrating member mounts the retractor blades to the tissue.

24. The surgical apparatus according to claim 22 wherein the actuator member is mounted to the handle portion and operatively engageable with the retractor blades and the tissue penetrating member, wherein, in a first mode of operation of the actuating member, movement of the actuator member causes relative movement of the two retractor blades and wherein, in a second mode of operation of the actuator member, movement of the actuator member causes movement of the tissue penetrating member to the deployed position.

25. The surgical apparatus according to claim 24 including a control member movable to selectively move the actuator member between the first and second modes of operation.

26. The surgical apparatus according to claim 22 including first and second retractor blades, the first retractor blade being movable relative to the second retractor blade and operatively connected to the actuator member.

27. A surgical apparatus, which comprises:

a) a handle portion dimensioned to be grasped by the hands of a user;

b) an elongated portion connected to the handle portion and extending distally therefrom, the elongated portion defining a longitudinal axis and having proximal and distal end portions;

c) at least two retractor blades supported for articulating movement at the distal end portion of the elongated portion and being adapted for relative movement; and d) a tissue penetrating member operatively associated with the retractor blades and releasably mounted to the distal end portion of the elongated portion, the tissue penetrating member movable to a deployed position to engage tissue.

28. The surgical apparatus according to claim 27 wherein the retractor blades are articulatable through a range from about 0° to about 90° relative to the longitudinal axis.

29. A method for facilitating the retracting of tissue during a surgical procedure, comprising the steps of:

a) accessing the targeted tissue area;

b) positioning a surgical instrument adjacent the tissue area, the surgical instrument including an elongated portion, a retractor mechanism having at least two retractor blades releasably mounted to the elongated portion and a proximally positioned actuator operatively connected to the retractor blades and movable relative to the elongated portion, and a tissue penetrating member releasably mounted to the elongated portion;

c) actuating the retractor mechanism by moving the proximally positioned actuator relative to the elongated portion to cause relative movement of the retractor blades such that the retractor blades engage and retract tissue to enhance access to a desired tissue area;

d) mounting the tissue penetrating member associated with the retractor blades within tissue;

e) releasing the retractor blades and the tissue penetrating member from the elongated portion of the surgical instrument whereby the retractor blades are retained within the tissue by the tissue penetrating member; and f) performing a surgical procedure.

30. The method according to claim 29 wherein the surgical instrument includes a release mechanism associated with the retractor blades and the tissue penetrating member and wherein the step of releasing includes actuating the release mechanism to release the retractor blades and the tissue penetrating member.

31. The method according to claim 30 wherein the release mechanism includes a proximally positioned release member and wherein the step of releasing includes moving the release member to cause actuation of the release mechanism.

32. The method according to claim 29 wherein the step of performing a surgical procedure includes performing a laparoscopic discectomy procedure.

33. The method according to claim 32 wherein the step of actuating the retractor mechanism includes engaging and retracting spinal tissue with the retractor blades.

34. The method according to claim 33 wherein the step of mounting includes mounting the tissue penetrating member to a vertebral body.

35. The method according to claim 29 further including the step of retrieving the retractor blades and the tissue penetrating member subsequent to the step of performing the surgical procedure.

36. A method for facilitating the retracting of tissue during a surgical procedure, comprising the steps of:

a) accessing the targeted tissue area;

b) positioning a surgical instrument adjacent the tissue area, the surgical instrument including an elongated portion, a retractor mechanism having at least two retractor blades releasably mounted to the elongated portion, a tissue penetrating member releasably mounted to the elongated portion and an articulating mechanism associated with the retractor blades and further including the step of;

c) actuating the articulating mechanism to selectively articulate the retractor blades;

d) actuating the retractor mechanism to cause relative movement of the retractor blades such that the retractor blades engage and retract tissue to enhance access to a desired tissue area;

e) mounting the tissue penetrating member associated with the retractor blades within tissue;

f) releasing the retractor blades and the tissue penetrating member from the elongated portion of the surgical instrument whereby the retractor blades are retained within the tissue by the tissue penetrating member; and g) performing a surgical procedure.

37. The method according to claim 36 wherein the retractor blades are connected to the distal end of the elongated portion by a connector member, the connector member including a memory material, and being movable between a generally linear stressed condition and a curved unstressed condition, and wherein the step of actuating the articulating mechanism includes moving the connector member to the curved unstressed condition whereby the retractor blades are positioned in articulated relation with respect to the longitudinal axis.

38. A method for performing a laparoscopic discectomy, comprising the steps of:

endoscopically accessing the vertebral column through an anterior endoscopic port;

inserting a surgical instrument through the endoscopic port, the instrument including an elongated portion, a retractor mechanism having at least two retractor blades releasably mounted to the elongated portion, and a tissue penetrating member associated with the retractor blades and releasably mounted to the elongated portion;

actuating the retractor mechanism to cause relative movement of the retractor blades such that the retractor blades engage and retract tissue to permit access to an underlying intervertebral disc;

deploying the tissue penetrating member to cause the tissue penetrating member to penetrate the vertebral body;

releasing the retractor blades and the tissue penetrating member from the elongated portion whereby the tissue penetrating member is mounted to the vertebral body and the retractor blades are retained within tissue by the tissue penetrating member; and removing at least a portion of the disc nucleus of the disc.

39. A surgical apparatus, which comprises:

a) a handle portion dimensioned to be grasped by the hand of a user;

b) an elongated portion connected to the handle portion and extending distally therefrom, the elongated portion defining a longitudinal axis and having proximal and distal end portions;

c) at least two retractor members supported for articulating movement at the distal end portion of the elongated portion and being further adapted for relative movement;

d) a tissue penetrating member operatively associated with the retractor members and releasably mounted to the distal end portion of the elongated portion;

e) a first manually operable member mounted to the handle portion and operatively connected to the retractor members, the first operable member movable relative to the handle portion to selectively articulate the retractor members;

f) a second manually operable member mounted to the handle portion and operatively connected to the retractor members, the second operable member movable relative to the handle portion to cause relative movement of the retractor members; and g) a third manually operable member mounted to the handle portion and operatively connected to the tissue penetrating member, the third operable member movable relative to the handle portion to release the tissue penetrating member from the elongated portion.

40. The surgical apparatus according to claim 39 wherein the tissue engaging member is longitudinally movable relative to the elongated portion from a non-deployed position to a deployed position to engage tissue.

41. The surgical apparatus according to claim 40 wherein the second operable member is operatively connected to the tissue penetrating member.

42. The surgical apparatus according to claim 41 wherein the second operable member is operable between first and second modes of operation, wherein, in the first mode of operation, movement of the second operable member causes relative movement of the retractor members and wherein, in the second mode of operation, movement of the second operable member causes movement of the tissue penetrating member to the deployed position thereof.

* * * * *